(12) United States Patent
Biradar et al.

(10) Patent No.: US 10,960,173 B2
(45) Date of Patent: Mar. 30, 2021

(54) RECOMMENDATION BASED ON DOMINANT EMOTION USING USER-SPECIFIC BASELINE EMOTION AND EMOTION ANALYSIS

(71) Applicant: SONY CORPORATION, Tokyo (JP)

(72) Inventors: Poornima Biradar, Bangalore (IN); Santhosh Ramegowda, Bangalore (IN); Jaison Joseph, Bangalore (IN)

(73) Assignee: SONY CORPORATION, Tokyo (JP)

(*) Notice: Subject to any disclaimer, the term of this patent is extended or adjusted under 35 U.S.C. 154(b) by 198 days.

(21) Appl. No.: 16/179,537

(22) Filed: Nov. 2, 2018

(65) Prior Publication Data
US 2020/0139077 A1    May 7, 2020

(51) Int. Cl.
| | | |
|---|---|---|
| A61M 21/00 | (2006.01) | |
| G10L 25/63 | (2013.01) | |
| G06K 9/00 | (2006.01) | |

(52) U.S. Cl.
CPC ......... *A61M 21/00* (2013.01); *G06K 9/00302* (2013.01); *G10L 25/63* (2013.01);
(Continued)

(58) Field of Classification Search
CPC ...... A61M 2205/60; A61M 2205/3306; A61M 21/00; A61M 2205/3375; A61M 2205/52;
(Continued)

(56) References Cited

U.S. PATENT DOCUMENTS

2001/0056349 A1    12/2001   St. John
2014/0089399 A1    3/2014    Chun et al.
(Continued)

FOREIGN PATENT DOCUMENTS

| AU | 7113000 A | 3/2001 |
|---|---|---|
| CN | 104423574 A | 3/2015 |

(Continued)

OTHER PUBLICATIONS

International Search Report and Written Opinion of PCT Application No. PCT/IB2019/058624, dated Dec. 11, 2019, 19 pages.
(Continued)

*Primary Examiner* — Christine H Matthews
*Assistant Examiner* — Joshua Daryl D Lannu
(74) *Attorney, Agent, or Firm* — Chip Law Group

(57) ABSTRACT

Electronic apparatus that stores user information received from a plurality of sensor that tracks user activities of a user over a specified time period. The electronic apparatus includes circuitry that detects a baseline emotion of the user based on the user information. The circuitry detects a dominant emotion of the user based on a change in an emotional characteristic of the user and the detected baseline emotion. The circuitry further recommends content and an emotional storyboard to the user based on specified emotion associated with the content, the baseline emotion, and the dominant emotion. The recommended content and the emotional storyboard is to induce a change in an emotional type of the dominant emotion from a negative emotional type to a positive emotional type.

19 Claims, 14 Drawing Sheets

(52) U.S. Cl.
CPC ........... *A61M 2021/005* (2013.01); *A61M 2021/0027* (2013.01); *A61M 2205/3303* (2013.01); *A61M 2205/3306* (2013.01); *A61M 2205/3375* (2013.01); *A61M 2205/3584* (2013.01); *A61M 2205/52* (2013.01); *A61M 2205/60* (2013.01); *A61M 2209/088* (2013.01); *A61M 2230/06* (2013.01); *A61M 2230/63* (2013.01)

(58) Field of Classification Search
CPC .... A61M 2205/3584; A61M 2209/088; A61M 2230/63; A61M 2205/3303; A61M 2230/06; A61M 2021/0027; A61M 2021/005; G06K 9/00302; G06F 3/011; G06F 2203/011; G10L 25/63
See application file for complete search history.

(56) References Cited

U.S. PATENT DOCUMENTS

| | | | |
|---|---|---|---|
| 2015/0058615 A1 | 2/2015 | Lee | |
| 2015/0254563 A1 | 9/2015 | Lynar et al. | |
| 2015/0332166 A1* | 11/2015 | Ferens | G06F 3/011 706/11 |
| 2016/0070245 A1 | 3/2016 | Lee et al. | |
| 2017/0337476 A1 | 11/2017 | Gordon et al. | |
| 2018/0075490 A1* | 3/2018 | Chintalapoodi | H04N 21/4668 |

FOREIGN PATENT DOCUMENTS

| | | | | |
|---|---|---|---|---|
| CN | 105453070 A | 3/2016 | | |
| CN | 107205731 A | 9/2017 | | |
| CN | 107807947 A | 3/2018 | | |
| CN | 109154861 A | 1/2019 | | |
| EP | 2840464 A1 * | 2/2015 | ......... | G06F 11/3419 |
| EP | 2840464 A1 | 2/2015 | | |
| EP | 3047387 A1 | 7/2016 | | |
| EP | 3293691 A1 | 3/2018 | | |
| EP | 3458940 A1 | 3/2019 | | |
| JP | 6547977 B2 | 7/2019 | | |
| KR | 10-2015-0021842 A | 3/2015 | | |
| KR | 10-2016-0029375 A | 3/2016 | | |
| KR | 10-2018-0028939 A | 3/2018 | | |
| WO | 01/16892 A1 | 3/2001 | | |
| WO | 2015/041668 A1 | 3/2015 | | |
| WO | 2017/200855 A1 | 11/2017 | | |

OTHER PUBLICATIONS

Yussa, et al., "A Negotiation Support Tool Using Emotional Factors", IEEE Conference Publication, Proceedings Joint 9th IFSA World Congress and 20th NAFIPS International Conference, Jul. 25-28, 2001, 01 page.

Kouris Kalligas, "Why Emotion Tracking is Important", Aug. 1, 2017, 10 pages.

* cited by examiner

| Time stamp 702 | Trigger 704 | User Emotion 706 | User Information 708 |
|---|---|---|---|
| 10 AM to 1 PM | - Watching News - Listening to Sad Music | 😊 😐 😕 ☹️ | Temp: XXX BP: XXX Heartbeat: XX ⋮ |
| 3PM To 8PM | Lunch Supervisor in proximity Stormy Weather | 😊 😐 ☹️ | Temp: XXX BP: XXX Heartbeat: XX ⋮ |
| ⋮ | ⋮ | ⋮ | ⋮ |

FIG. 7A

RECOMMENDATION BASED ON DOMINANT EMOTION USING USER-SPECIFIC BASELINE EMOTION AND EMOTION ANALYSIS

CROSS-REFERENCE TO RELATED APPLICATIONS/INCORPORATION BY REFERENCE

None.

FIELD

Various embodiments of the disclosure relate to timeline based emotion tracking and analysis technologies and content recommendation technologies. More specifically, various embodiments of the disclosure relate to an electronic apparatus and a method to recommend a specific content based on detection and analysis of dominant emotion and user-specific baseline emotion.

BACKGROUND

Recent advancement in the field of human emotion detection have led to development of various technologies to monitor emotion of a user. Different users may respond differently to a given situation. Further, it is observed that an emotion is manifested on a user's face, behavior, or in presence of another individual in a given situation, is also specific for a specific user. Existing technology to detect emotions typically set blanket emotion detection rules that are almost the same for all users, and are thus not effective and accurate enough in emotion tracking for different users. Further, certain conventional solutions, which continuously monitor the emotion of a specific user, may lack an intelligent or enabling technology to improve an emotional state of the user. Thus, an advanced system may be desired to monitor emotion state of the user in detail, and provide technological solutions to improve the emotional state as well as health state specific to the user.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

An electronic apparatus and method to provide recommendation based on dominant emotion using user-specific baseline emotion and emotion analysis is provided substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

BRIEF DESCRIPTION OF THE DRAWINGS

FIGS. 7A, 7B, and 7C, collectively, illustrate exemplary second user interface to display an emotional storyboard, in accordance with an embodiment of the disclosure.

DETAILED DESCRIPTION

The following described implementations may be found in the disclosed system to recommend content or action based on dominant emotion detection and user-specific baseline emotion. The disclosed system includes an electronic apparatus that processes user information over a specified time period to create a detailed emotional timeline and recommend appropriate content or action to improve an emotional state of the user. The disclosed electronic apparatus provides a mechanism that supports identifying a baseline emotion of a user, monitors key emotions, and changes in emotions of users over time. The disclosed electronic apparatus generates an insightful analysis as an emotional journey for a particular user so that the user is able to assess not only the moments triggering emotional peaks but also related recommendations to improve the emotional state of the user over time. Emotion triangle technology is also disclosed that involves identifying an emotion of the content or action recommended, emotion of the user, and the emotion, which the content or the action can invoke in a viewer. The electronic apparatus further analyses and determines dominant emotion of a user by baselining (i.e., user-specific baseline emotion determination) the user's emotion and identifying certain peaks in the emotion changes along with an intensity of the user's emotion. This enables the electronic apparatus to output a highly effective content or action recommendations and assists users to achieve and manage a better emotional health and reduces impact of negative emotions. The disclosed electronic apparatus assists different user to be conscious of their own emotional triggers and emotional peaks in a specific context or a given situation that may be specific to a user.

Figure 1:
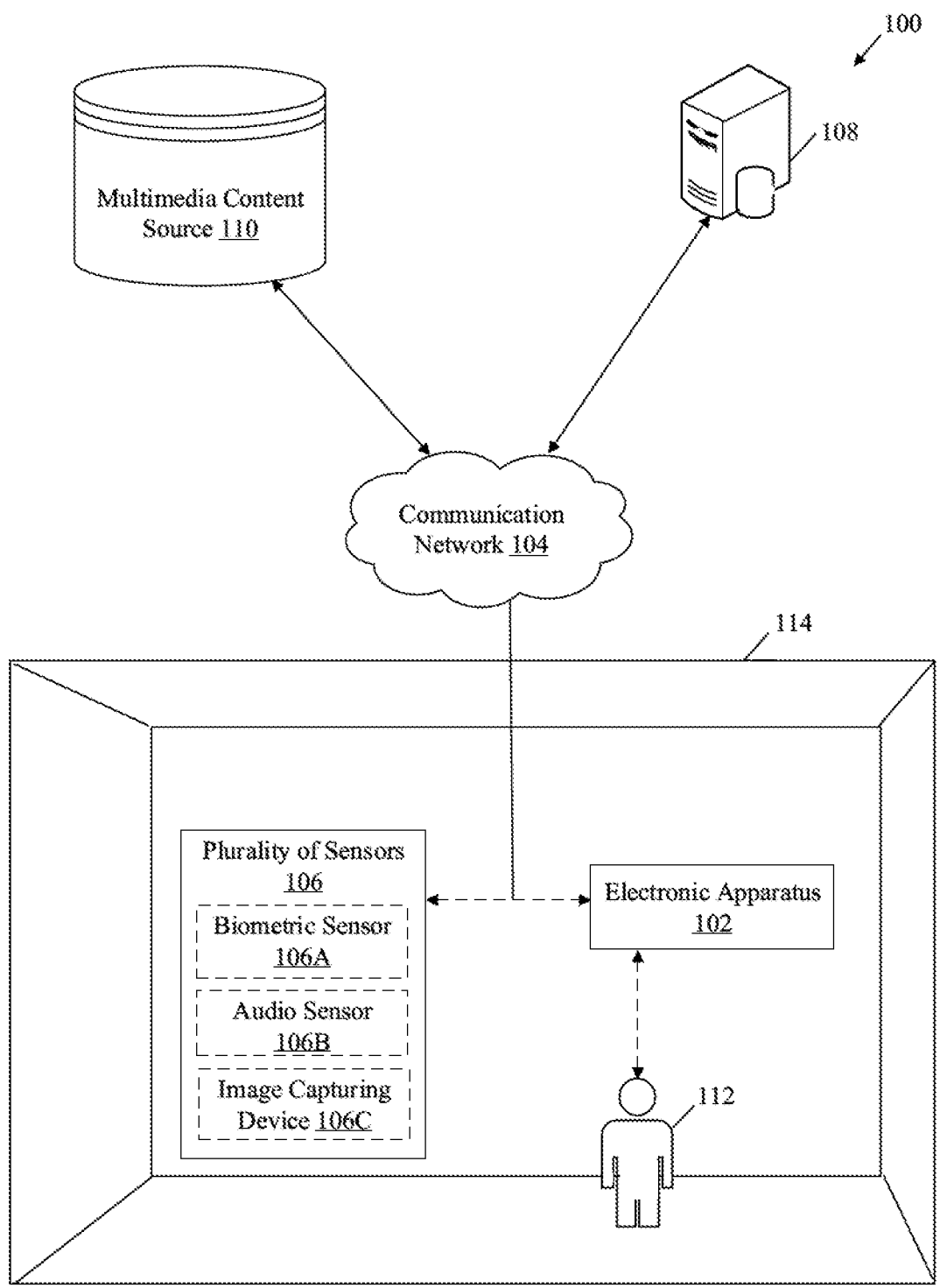
FIG. 1 is a block diagram that illustrates an exemplary network environment for generating an emotional storyboard and recommending content or action, in accordance with an embodiment of the disclosure.

FIG. 1 is a block diagram that illustrates an exemplary network environment to generate an emotional storyboard and recommend content or action, in accordance with an embodiment of the disclosure. With reference to FIG. 1, there is shown a network environment 100. The network environment 100 may include an electronic apparatus 102, a communication network 104, and a plurality of sensors 106, a server 108, and a multimedia content source 110. The electronic apparatus 102 may be communicatively coupled to the plurality of sensors 106, the server 108, and the multimedia content source 110 via the communication network 104. There is further shown a user 112 associated with the electronic apparatus 102 in a three-dimensional (3D) space 114.

The electronic apparatus 102 may include suitable logic, circuitry, and interfaces that may be configured to capture user information of the user 112 from the plurality of sensors 106 over a specified time period. The electronic apparatus 102 may be further configured to analyze the user information to generate an emotional storyboard of the user's emotion and recommend content or action to the user 112. The electronic apparatus 102 may be configured to receive the recommended content or information with respect to action from the multimedia content source 110 through the communication network 104. In accordance with an embodiment, the electronic apparatus 102, the plurality of sensors 106, and the user 112 may be present in the 3D space 114. Examples of the electronic apparatus 102 may include a health monitoring system, a surveillance device, an electronic voice assistant, an audio-visual virtual assistant, a wearable device, an artificial intelligence (AI) system, a mobile phone, an audio-video reproduction apparatus, a special-purpose device, a laptop computer, a video-conferencing system, a computing device, a gaming device, a mainframe machine, a server, a computer work-station, a consumer electronic (CE) device, or a media processing system.

The communication network 104 may include a communication medium through which the electronic apparatus 102 may be communicatively coupled to the plurality of sensors 106, the server 108, and the multimedia content source 110. Examples of the communication network 104 may include, but are not limited to, the Internet, a cloud network, a Wireless Fidelity (Wi-Fi) network, a Personal Area Network (PAN), a Local Area Network (LAN), or a Metropolitan Area Network (MAN). Various devices in the network environment 100 may be configured to connect to the communication network 104, in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity(Li-Fi), 802.16, IEEE 802.11s, IEEE 802.11g, multi-hop communication, device to device communication, cellular communication protocols, and Bluetooth (BT) communication protocols.

The plurality of sensors 106 may include suitable logic, circuitry, and interface that may be configured to capture the user information of the user 112. The user information may correspond to emotional data of the user 112. The plurality of sensors 106 may include, but are not limited to a biometric sensor 106A, an audio sensor 106B, and an image capturing device 106C. The biometric sensor 106A may be configured to capture biometric data, as the user information, of the user 112. Examples of the biometric sensor 106A may include, but are not limited to, a pulse rate sensor, a breath rate sensor, a body temperature sensor, a heartbeat sensor, a blood-flow sensor, an IoT sensor or a skin conductance sensor, or other specialized sensors to measure different emotions aroused in the user 112. In some embodiments, the biometric sensor 106A may be non-invasively attached to body of the user 112. In some embodiments, the biometric sensor 106A may be invasively implanted inside the body of the user 112. In some embodiments, the biometric sensor 106A may be installed in the 3D space 114, to collectively monitor the biometric data of the user 112.

The audio sensor 106B may be configured to capture voice data of the user 112 over the specified time period. The captured voice data may be a part of the user information. The audio sensor 106B may be positioned on the body of the user 112 or may be positioned at a plurality of locations within the 3D space 114. Examples of the audio sensor 106B may include, but are not limited to, a microphone or other audio capturing device known in the art.

The image capturing device 106C may be configured to capture a plurality of images of the user 112 over the specified time period. The captured plurality of images may be utilized to determine a facial expression of the user 112 based on which an emotional state of the user 112 may be determined for the specified time period. The image capturing device 106C may be positioned at any location in the 3D space 114 to capture the plurality of image frames of the user 112. In accordance with an embodiment, the position of the image capturing device 106C may be changeable. Examples of the image capturing device 106C may include, but are not limited to, an image sensor, a wide-angle camera, an action camera, a closed-circuit television (CCTV) camera, a camcorder, a time-of-flight camera (TOF camera), a night-vision camera such as Infrared (IR) camera, and/or other image capturing devices. In accordance with an embodiment, the plurality of sensors 106 may be integrated in the electronic apparatus 102. In accordance with an embodiment, the image capturing device 106C may comprise a Global Positioning System (GPS) configured to detect current location of the electronic apparatus 102. The electronic apparatus 102 may be configured to identify environmental conditions (for example temperature, humidity, rainfall) around the electronic apparatus 102 or the user 112 based on the detected current location. In accordance with an embodiment, the electronic apparatus 102 may be configured to receive information related to the environmental conditions from the server 108 based on the detected current location.

The server 108 may include suitable logic, circuitry, and interfaces that may be configured to store user information of the user 112. The user information may include user-profile information, user-content preference information, an event calendar, and past emotional information of the user 112. In accordance with an embodiment, the server 108 may be configured to store and continuously update an emotional storyboard of the user 112 generated in past. In accordance with an embodiment, the server 108 may be configured to provide the stored information related to the user 112, and stored emotional storyboard to the electronic apparatus 102 through the communication network 104. In some embodiments, the server 108 may be implemented as a cloud server, which may be utilized to execute aforementioned operations of the server 108 through web applications, cloud applications, HTTP requests, repository operations, file transfer, gaming operations, and the like. Other examples of the server include, but are not limited to a database server, a file server, a web server, an application server, a mainframe server, a cloud server, or other types of server.

The multimedia content source 110 may include suitable logic, circuitry, and interfaces that may be configured to store multimedia content. Examples of the multimedia content may include, but are not limited to, audio content, video content, animation content, and/or interactive content. The interactive content may comprise, but is not limited to augmented reality (AR), virtual reality (VR), mixed reality (MR), or extended reality (XR). In accordance with an embodiment, the multimedia content source 110 may be configured to provide the stored multimedia content to the electronic apparatus 102 via the communication network 104 based on a request for content received from the electronic apparatus 102 or the server 108. In some embodiments, the multimedia content source 110 may be a server which may be configured to store the multimedia content. In some embodiments, the multimedia content source 110 may be implemented as a cloud server, which may be utilized to execute aforementioned operations of the multimedia content source 110 through web applications, cloud applications, HTTP requests, repository operations, file transfer, gaming operations, and the like. Other examples of the server include, but are not limited to a database server, a file server, a web server, an application server, a mainframe server, a cloud server, or other types of server.

The 3D space 114 may refer to a 3D area in which the electronic apparatus 102, user 112 and the plurality of sensors 106 are present. Examples of the 3D space 114 may include, but are not limited to, a physical space within room or a building (such as an enclosed residential space, a movie theater, a conference area, and the like), or a combination of the open space and built architectures (e.g., a stadium, an outdoor musical event, a park, a playground, and the like).

In operation, the plurality of sensors 106 may be configured to track user activities of the user 112 over a specified period of time (such as in hours, days, weeks, months or years). In accordance with an embodiment, the electronic apparatus 102 may be configured to receive the user information from the plurality of sensors 106 via the communication network 104. The user information may include the biometric data, voice data, the plurality of images (including facial expression) of the user 112, the current location of the electronic apparatus 102, and the information related to environmental conditions around the electronic apparatus 102 or the user 112.

In accordance with an embodiment, the electronic apparatus 102 may be configured to store the user information of the user 112 in the electronic apparatus 102. The electronic apparatus 102 may be further configured extract (or detect) a baseline emotion of the user 112 based on the user information. The baseline emotion may be an initial baseline emotion which may correspond to a neutral emotion of the user 112. The neutral emotion may be further updated by the electronic apparatus 102 over a first time period in the specified time period to obtain the actual baseline emotion of the user 112. In some embodiments, the baseline emotion of the user 112 may correspond to a natural or usual emotion (or behavior) of the user 112. In accordance with an embodiment, the electronic apparatus 102 may be configured to detect the baseline emotion based on the plurality of categories of user emotions stored in the electronic apparatus 102. The plurality of categories of user emotions may include, but are not limited to, a happy emotion, a sad emotion, an angry emotion, a calm emotion, a fear emotion, a neutral emotion, an excited emotion, a confused emotion, a stressed emotion, a disgusted emotion, a surprised emotion, an excitement emotion, or a scared emotion. In some embodiments, the plurality of categories of user emotions may be identified based on, but are not limited to, human emotions as mentioned in Plutchik wheel of emotions, Lövheim cube of emotion, PAD emotional state model, Positive activation-negative activation (PANA) model, circumplex model, vector model, Plutchik's wheel in Venn format, Parrott's emotions or the Hourglass of Emotions. In accordance with an embodiment, the electronic apparatus 102 may be configured to receive the plurality of categories of user emotions from the server 108 via the communication network 104.

The electronic apparatus 102 may be further configured to monitor and detect a change in an emotion characteristic of the user 112 over a second time period in the specified time period based on the user information. The second time period may be different from the first time period. For example, after the baseline emotion of a specific user is known, then the change in the emotion characteristics may be detected effectively. If the change is detected before the baseline emotion detection, then the detected change may be erroneous. The emotional characteristic of the user 112 may correspond to a category of emotion in the plurality of categories of user emotions. In accordance with an embodiment, the electronic apparatus 102 may be configured to detect intensity levels of the emotional characteristic of the user 112. The electronic apparatus 102 may be further configured to detect an emotional peak of the detected intensity levels in the emotion characteristic of the user 112 based on a set threshold intensity of the emotional characteristic. The electronic apparatus 102 may be further configured to determine a dominant emotion of the user 112 based on the detected change in the emotional characteristic of the user 112, the detected emotional peak, and the baseline emotion. In accordance with an embodiment, the electronic apparatus 102 may be configured to update the baseline emotion (e.g. which may be initially neutral or self-information provided by the user 112) with the detected dominant emotion. The detection of the dominant emotion of the user 112 based on the user information (received from the plurality of sensor 106) may be described in detail, for example, in FIGS. 3A to 3B.

In accordance with an embodiment, the electronic apparatus 102 may be further configured to identify an emotional type of the determined dominant emotion. The emotional type is one of a positive emotional type (such as happy emotion) or a negative emotional type (such as sad or angry emotion). The electronic apparatus 102 may be further configured to generate deductive information based on an association of the identified emotional type of the dominant emotion, the determined dominant emotion of the first user, the first change in the emotional characteristic of the first user, and the detected baseline emotion. The deductive information may be an insight or new supplemental information not present previously in the electronic apparatus 102, where the deductive information is used as control instructions for various operations. For example, the electronic apparatus 102 may be configured to identify first content or action based on a specified emotion associated with the first content or action, and the generated deductive information. In some embodiments, the deductive information may be generated based on artificial intelligence (AI) and its variants applied on the user information, the identified emotional type of the dominant emotion, the determined dominant emotion of the first user, the first change in the emotional characteristic of the first user, and the detected baseline emotion to deduce a relationship among different data points and find insights. The first content may include, but are not limited to, audio content, video content, image content, animated content, multimedia content. The action identified by the electronic apparatus 102 or recommended to the user 112 may include, but are not limited to, an activity-to-do or place-to-visit.

In accordance with an embodiment, the electronic apparatus 102 may be configured to send the request for content or action to the multimedia content source 110 for the identified first content or action via the communication network 104. The electronic apparatus 102 may be further configured to receive the identified first content or action from the multimedia content source 110 via the communication network 104. In accordance with an embodiment, the electronic apparatus 102 may be further configured to identify the first content or action based on user-content preference information, the event calendar, and past emotional information of the user 112. The electronic apparatus 102 may be configured to receive the user-content preference information and the past emotional information of the user 112 from the server 108 via the communication network 104.

In accordance with an embodiment, the electronic apparatus 102 may be configured to identify the first content or action with an intent to change the emotion type of the dominant emotion of the user 112 from the negative emotional type to the positive emotional type. The electronic apparatus 102 may be configured to control output of the identified first content or action to the user 112 based on a specified emotion associated with the first content or action and the generated deductive information such that the emotional type of the dominant emotion is inducible to the positive emotional type from the negative emotional type. The output of the identified first content or action may be controlled on a display screen or the audio output device for user consumption (e.g., of the user 112). In some embodiment, the output of the first content or action on the display screen may be a haptic output or a virtual reality (VR) output. The output of the first content or action may improve current health status of the user 112. In accordance with an embodiment, the electronic apparatus 102 may be configured to analyze the emotional characteristic of the user 112 after the output of the first content or action to determine the emotion manifested in the user 112 based on the consumption of the first content or execution of the action.

The electronic apparatus 102 may be configured to store the emotions of the user 112 captured over the specified time period and generate a detailed emotional storyboard of the user 112. The emotional storyboard may include an emotional timeline of the user 112. The electronic apparatus 102 may be configured to output the generated emotional storyboard to the user 112 through the display screen and AR/VR mediums. A graphical representation of the generated emotional storyboard is described in detail, in FIGS. 7A to 7C. In some embodiments, the emotional storyboard may include information related different triggers which would have caused the change in the emotional characteristic of the user 112 over the specified time period. The triggers may include, but are not limited to, second content the user 112 may be viewing (or listening) or action the user 112 may be performing during the specified time period, events associated with the user 112 during the specified time period, or related people and surrounding environment around the user 112 that may influence the user 112 during the specified time period. The surrounding environment may be detected based on the information related environmental conditions around the electronic apparatus or the user 112. Information related to the different triggers may be described in detail, for example in FIG. 5. Thus, the disclosed electronic apparatus 102 may perform the detailed analysis of the user information of the user 112 for the specified time period which may vary from certain days to months or years. The detailed analysis of the user information and output of the dominant emotion (with relevant triggers) through the generated emotional storyboard may facilitate the user 112 to accurately understand the user's emotional patterns or changes specific to the user 112 over the specified time period. Further, accurate recommendation of the first content or action by the electronic apparatus 102 based on the detailed analysis of the user information and the generated emotional storyboard may further ensure an improvement in the emotional quotient of the user 112. Such improvement in the emotional quotient may further assist the user 112 to improve health status and fitness over time.

Figure 2:
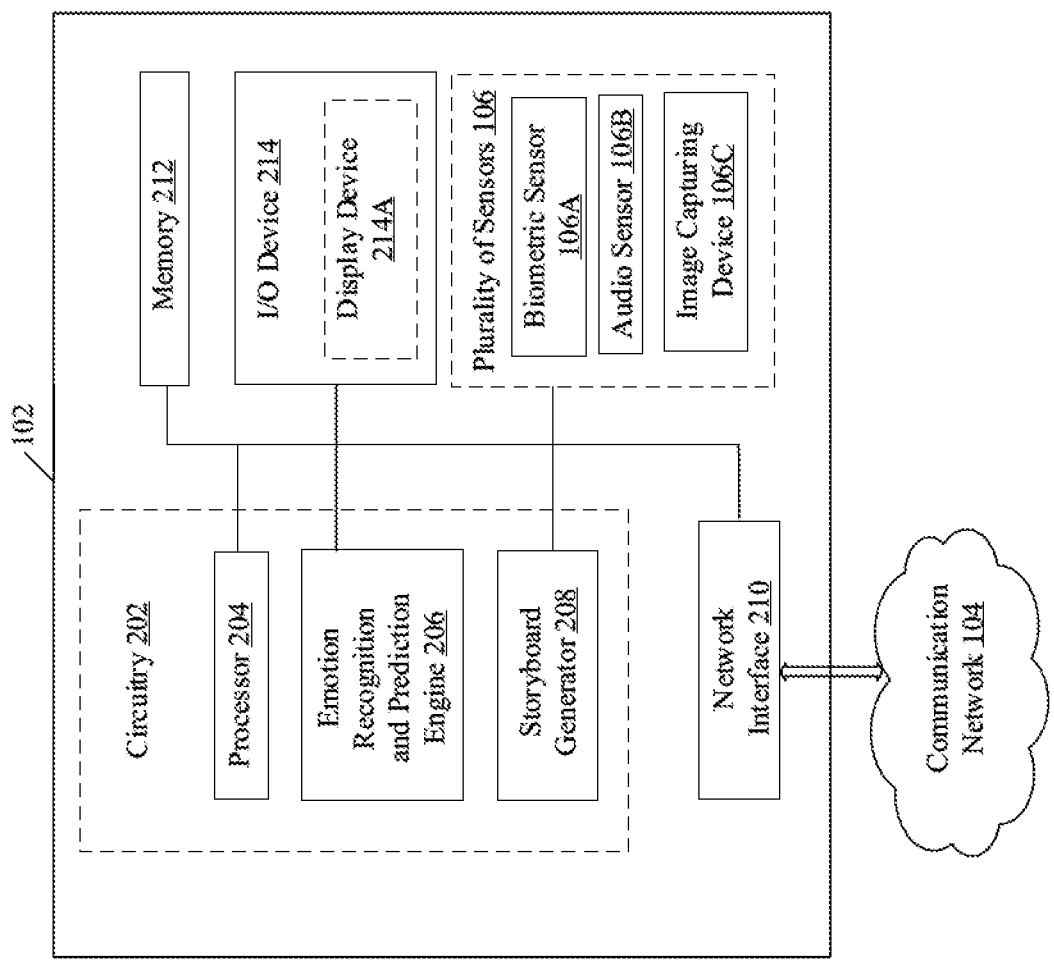
FIG. 2 is a block diagram that illustrates an exemplary electronic apparatus for generating an emotional storyboard and recommending content or action, in accordance with an embodiment of the disclosure.

FIG. 2 is a block diagram that illustrates an exemplary electronic apparatus for generating an emotional storyboard and recommending content or action, in accordance with an embodiment of the disclosure. FIG. 2 is explained in conjunction with elements from FIG. 1. With reference to FIG. 2, there is shown a block diagram of the electronic apparatus 102. The electronic apparatus 102 may include circuitry 202 that may include a processor 204, an emotion recognition and prediction engine 206, and an emotional storyboard generator 208. There is further shown a network interface 210, a memory 212, an Input/output (I/O) device 214, and the plurality of sensors 106 of FIG. 1. The I/O device 214 may include a display device 214A. The plurality of sensors 106 may include the biometric sensor 106A, the audio sensor 106B, and the image capturing device 106C. The circuitry 202 may be communicatively coupled with the network interface 210, the memory 212, the I/O device 214, and the plurality of sensors 106, via a set of communication ports/channels.

The processor 204 may include suitable logic, circuitry, and interfaces that may be configured to execute a set of instructions stored in the memory 212. The processor 204 may be configured to read the user information stored in the memory 212. In some embodiments, the processor 204 may be configured to receive the user information from the plurality of sensors 106. In some embodiments, the processor 204 may be configured to control the plurality of sensors 106 to track the user activities and provide the user information. The processor 204 may be further configured to receive user emotions associated with a plurality of categories of user emotions, the user-content preference information and the past emotional information of the user 112 from the server 108 via the network interface 210. The processor 204 may be further configured to receive the first content or the information related to the action from the multimedia content source 110 via the network interface 210. The processor 204 may be further configured to output the received first content or the information related to the action to the user 112 through the I/O device 214. In some embodiments, the processor 204 may be configured to request the multimedia content server 110 to stream content (such as the first content or the information related to the action) in real time to a device associated with the user 112. In some embodiments, the processor 204 may be embedded with the plurality of sensors 106 such as e-sensors. The processor 204 may be implemented based on a number of processor technologies known in the art. Examples of the processor 204 may include, but are not limited to, a Graphical Processing Unit (GPU), a Central Processing Unit (CPU), an x86-based processor, an x64-based processor, a Reduced Instruction Set Computing (RISC) processor, an Application-Specific Integrated Circuit (ASIC) processor, a Complex Instruction Set Computing (CISC) processor, low power deep neural network (DNN).

The emotion recognition and prediction engine 206 may include suitable logic, circuitry, and/or interfaces that may be configured to receive the user information of the user 112 from the processor 204. The emotion recognition and prediction engine 206 may be further configured to detect the emotions of the user 112 (such as happy, sad, angry, neutral or other possible emotions) based on the user information of the user 112 and the plurality of categories of user emotions. The emotion recognition and prediction engine 206 may be further configured to detect the baseline emotion of the user 112 for the specified time period. In accordance with an embodiment, the emotion recognition and prediction engine 206 may be further configured to detect the change in the emotional characteristic of the user 112. For example, the emotion recognition and prediction engine 206 may be further configured to detect a change in the facial expression or a change in breathing rate to detect the change in the emotional characteristic of the user 112. The emotion recognition and prediction engine 206 may be further configured to detect a change in the intensity levels of the emotional characteristic of the user 112 and set a threshold intensity of the emotional characteristic. The emotion recognition and prediction engine 206 may be further configured to detect the emotional peak of the intensity levels of the emotional characteristic based on the set threshold intensity. The emotion recognition and prediction engine 206 may be further configured to detect the dominant emotion as the changed emotion of the user 112 based on the detected emotional peak or the detected change in the emotional characteristic of the user 112.

In accordance with an embodiment, the emotion recognition and prediction engine 206 may be further configured to predict the emotion of the user 112 based the user-content preference information and the past emotional information of the user 112 associated with the user-content preference information. Examples of implementations of the emotion recognition and prediction engine 206 may be a specialized circuitry, an inference engine circuitry, a neural network circuitry, a co-processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), or other control circuits.

The emotional storyboard generator 208 may include suitable logic, circuitry, and/or interfaces that may be configured to receive the user information from the processor 204. The emotional storyboard generator 208 may be further configured to receive the detected emotions of the user 112, the baseline emotion, the detected dominant emotion and the triggers for change in the baseline emotion from the emotion recognition and prediction engine 206. The emotional storyboard generator 208 may be further configured to generate the emotional storyboard of the user 112 for the specified time period. The emotional storyboard may be an emotional timeline of the user's emotion for the specified time period. In accordance with an embodiment, the emotional storyboard may include the user information, the triggers for the change in the emotional characteristic of the user 112 in the specified time period. Examples of implementations of the emotional storyboard generator 208 may be a specialized circuitry, a Graphics Processing Unit (GPU), a co-processor, a Reduced Instruction Set Computing (RISC) processor, an Application-Specific Integrated Circuit (ASIC) processor, a Complex Instruction Set Computing (CISC) processor, a microcontroller, a central processing unit (CPU), or other control circuits.

The network interface 210 may include suitable logic, circuitry, and interfaces that may be configured to establish communication between the electronic apparatus 102, the server 108, and the multimedia content source 110, via the communication network 104. The network interface 210 may be implemented by use of various known technologies to support wired or wireless communication of the electronic apparatus 102 with the communication network 104. The network interface 210 may include, but is not limited to, an antenna, a radio frequency (RF) transceiver, one or more amplifiers, a tuner, one or more oscillators, a digital signal processor, a coder-decoder (CODEC) chipset, and a local buffer. In accordance with an embodiment, the network interface 210 may further include a subscriber identity module (SIM) card.

The memory 212 may include suitable logic, circuitry, and interfaces that may be configured to store a set of instructions executable by the processor 204. The memory 212 may be configured to store the user information captured by the plurality of sensors 106. In some embodiments, the memory 212 may be configured to store the plurality of categories of user emotions and their corresponding values of emotional characteristic. In some embodiments, the memory 212 may be configured to store the user-content preference information, the event calendar, the information related environmental conditions, and the past emotional information of the user 112. In some embodiments, the memory 212 may be configured to store a plurality of content items, such as the first content or the information related to the action, received from the multimedia content source 110 that to be recommended to the user 112. Examples of implementation of the memory 212 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, or a Secure Digital (SD) card.

The I/O device 214 may include suitable logic, circuitry, and interfaces that may be configured to provide an I/O channel/interface between the user 112 and the different operational components of the electronic apparatus 102. The I/O device 214 may receive an input from the user 112 and present an output based on the provided input from the user 112. The I/O device 214 may include various input and output ports to connect various other I/O devices that may communicate with different operational components of the electronic apparatus 102. Examples of the input device may include, but are not limited to, a touch screen, a keyboard/keypad, a set of buttons, a mouse, a joystick, a microphone, and an image-capture device. Examples of the output device may include, but are not limited to, a display (for example, the display device 214A), a speaker, and a haptic or any sensory output device.

The display device 214A may include suitable logic, circuitry, interfaces that may be configured to render an application interface at the display device 214A, to display the emotional storyboard and the recommended first content or the information related to the action to the user 112 operating the electronic apparatus 102. The display device 214A may be realized through several known technologies such as, but not limited to, at least one of a Liquid Crystal Display (LCD) display, a Light Emitting Diode (LED) display, a plasma display, and an Organic LED (OLED) display technology, and other display. In accordance with an embodiment, the display device 214A may refer to a display screen of smart-glass device that are compatible with the AR, VR, MR, and XR technologies, a see-through display, a projection-based display, an electro-chromic display, and a transparent display.

The functions or operations executed by the electronic apparatus 102, as described in FIG. 1, may be performed by the circuitry 202, such as the processor 204, the emotion recognition and prediction engine 206, and the emotional storyboard generator 208, which are further described, for example, in the FIGS. 3A, 3B, 4, 5A, 5B, 6, and 7A to 7C.

Figure 3A:
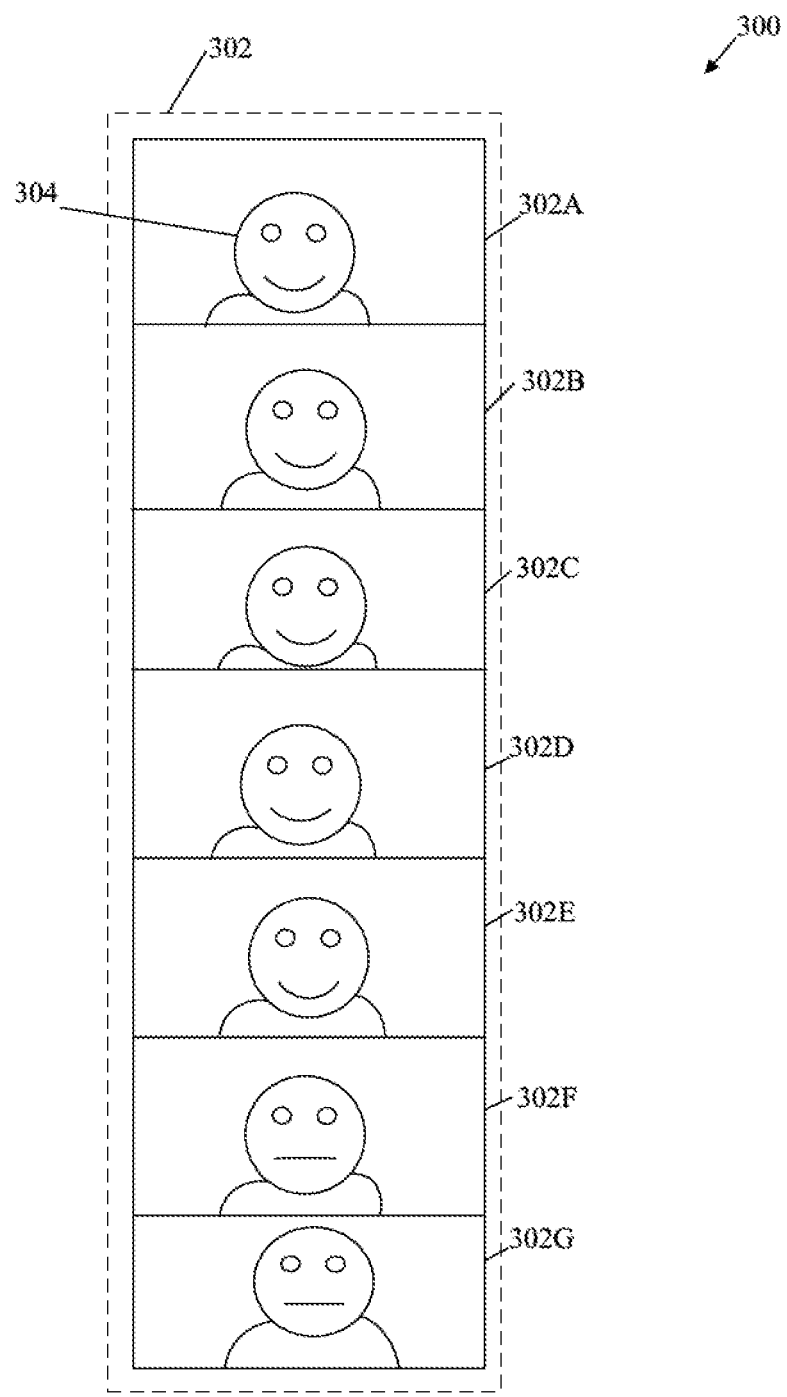
FIGS. 3A and 3B, collectively, illustrate exemplary operations for detection of baseline emotion and dominant emotion, by the electronic apparatus of FIG. 2, in accordance with an embodiment of the disclosure.
Figure 3B:
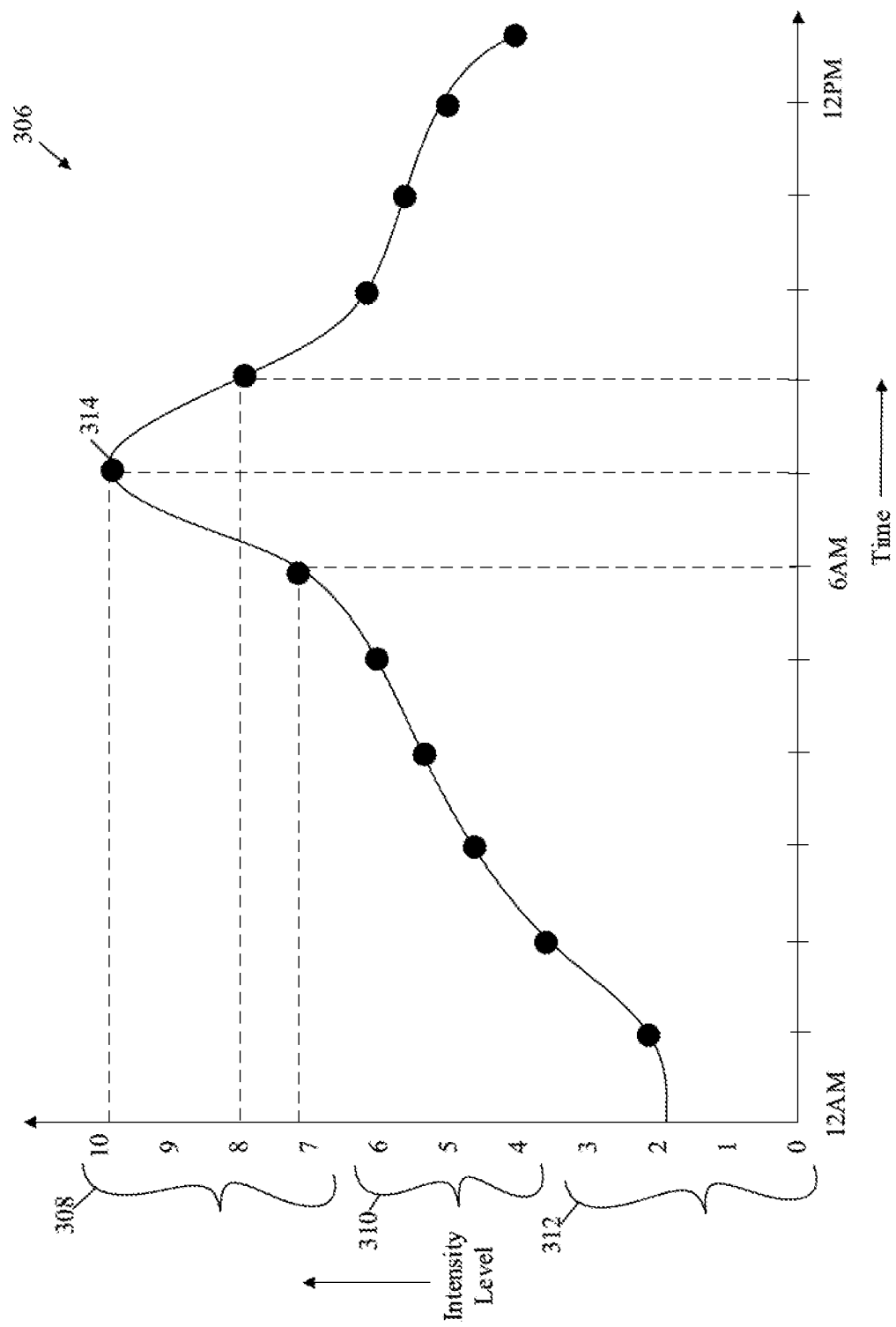

FIGS. 3A and 3B, collectively, illustrate exemplary operations for detection of baseline emotion and dominant emotion, in accordance with an embodiment of the disclosure. FIG. 3A is explained in conjunction with elements from FIGS. 1 and 2. With reference to FIG. 3A, there is shown a plurality of image frames 302. The plurality of image frames 302 may include image frames 302A to 302G captured by the image capturing device 106C over the specified time period. The image frames 302A to 302G may include an image 304 of the user 112. In some embodiments, the image frames 302A to 302G may include the facial expression in the user information of the user 112. The facial expression may indicate one or more motions or positions of muscles of a face of the user 112, where the facial expressions may manifest an emotion. The muscles of the face may move the skin of the user 112, may create facial lines/folds, or may cause the movement of facial features, such as mouth, head, nose, eye, eyebrows of the user 112. In accordance with an embodiment, the image frames 302A to 302G are consecutively captured by the image capturing device 106C over the specified time period.

In accordance with an embodiment, the emotion recognition and prediction engine 206 may be configured to detect the emotion of the user 112 in each of the image frames 302A to 302G captured over the specified time period. The specified time period may in minutes, hours, days, weeks, months, or years. In accordance with an embodiment, the electronic apparatus 102 may be configured to receive a user input from the user 112 to set the specified time period to track the user activities (or the user information). The emotion recognition and prediction engine 206 may be configured to determine the facial expressions of the user 112 and detect emotions based on the user information (such as the determined facial expressions) and the stored plurality of categories of user emotions. The categories of the user emotions may include, but are not limited to, a happy emotion, a sad emotion, an angry emotion, a calm emotion, a fear emotion, a neutral emotion, an excited emotion, a confused emotion, a stressed emotion, a disgusted emotion, a surprised emotion, an excitement emotion, a scared emotion, or a mixed emotion. In accordance with an embodiment, the emotion recognition and prediction engine 206 may be configured to match the detected facial expression with each of the plurality of categories of user emotions to determine the emotion of the user 112 in each of the image frames 302A to 302G. For example, in a set of image frames 302A to 302E, the detected emotion of the user 112 may be the happy emotion. The user 112 may be happy over the first time period in the specified time period. The emotion recognition and prediction engine 206 may be configured to set the baseline emotion of the user 112 as happy based on the detected emotion of the user 112 for the first time period. In some embodiments, the baseline emotion of the user 112 may correspond to natural or general emotion (or behavior) of the user 112. Although a number of image frames (e.g., the set of image frames 302A to 302E) are shown in the FIG. 3A, to detect a baseline emotion, image analysis by the emotion recognition and prediction engine 206 for a longer period of time, for example for one or more weeks, may provide more accurate understanding and detection of the baseline emotion.

In accordance with an embodiment, the plurality of categories of user emotions may include different values of biometric or voice data associated with each category of the plurality of categories of user emotions. For example, a value of heartbeat above 100 bpm (beats per minute) of the user 112 may be associated with the fear emotion or excitement emotion of the user 112. A volume of voice above 75 decibels (dB) may be associated with the anger emotion of the user 112. In accordance with an embodiment, the emotion recognition and prediction engine 206 may be further configured to detect the emotion of the user 112 based on comparison between different values in the user information captured from the plurality of sensors 106 and the values of biometric or voice data included with each category of the plurality of categories of user emotions.

The emotion recognition and prediction engine 206 may be further configured to detect the change in the emotional characteristic of the user 112. The emotional characteristic may indicate the detected emotion of the user 112 in each of the image frames 302A to 302G. For example, a first image frame 302E and a second image frame 302F of the image frames 302A to 302G may indicate the change in the emotional characteristic of the user 112 from the happy emotion to the neutral emotion. In accordance with an embodiment, the emotion recognition and prediction engine 206 may be further configured to detect a subsequent image frame 302G which is subsequent to the changed second image frame 302F to confirm the change in the emotional characteristic of the user 112. The emotion recognition and prediction engine 206 may be further configured to detect the change in the emotional characteristic of the user 112 over a second time period (different from the first time period). In accordance with an embodiment, the emotion recognition and prediction engine 206 may be further configured to detect the dominant emotion of the user, as the neutral emotion, based on the detected change in the emotional characteristic of the user 112 over the second time period. In accordance with an embodiment, the emotion recognition and prediction engine 206 may be further configured to update (or calibrate) the baseline emotion based on the dominant emotion. In accordance with an embodiment, the user information of the user 112 may include the biometric data or the voice data captured from the plurality of sensors 106. The emotion recognition and prediction engine 206 may be configured to detect the baseline emotion and the dominant emotion of the user 112 over the specified time period based on the captured biometric data or the voice data of the user 112. Thus, the electronic apparatus 102 may provide accurate detection of the emotional characteristics of the user 112 based on the combination of the biometric data, the voice data and the plurality of images in the user information of the user 112.

With reference to FIG. 3B, there is shown a graphical representation 306 of intensity levels of the emotion of the user 112 for a time period (e.g., 12 hours from 12 am to 12 pm). The graphical representation 306 of the emotion may indicate the different intensity levels of a particular emotion during the time period. For example, the intensity levels of the emotion may vary from a scale of "1 to 10". In accordance with an embodiment, the intensity levels of each emotion experienced by the user 112 may be divided into three categories as a high intensity 308, a medium intensity 310, and a low intensity 312. The low intensity 312 may correspond to "1 to 3" intensity level, the medium intensity 310 may correspond to "4 to 6" intensity level, and the high intensity 312 may correspond to "7 to 10" intensity levels.

The graphical representation 306 may further indicate an emotional peak 314 for the emotion of the user 112 during the time period (e.g., 12 hours duration). The emotional peak may be a highest intensity level of the emotion during the time period. In accordance with an embodiment, the emotional peak 314 may correspond to the change in the intensity levels of the baseline emotion or the emotion characteristic of the user 112 over the time period. The emotion recognition and prediction engine 206 may be configured to dynamically or statically set the threshold intensity for the emotional peak. The emotion recognition and prediction engine 206 may be configured to dynamically or statically set the threshold intensity for the emotional peak based on a range of the intensity levels over the time period. For example, the emotion recognition and prediction engine 206 may be configured to set the threshold intensity at a low level of 2, if the intensity levels of the baseline emotion is in range of 1 to 3 over the time period. Further, the emotion recognition and prediction engine 206 may be configured to set the threshold intensity at a high level of 8, if the intensity level of the baseline emotion is in a range of 7 to 10 over the time period. With reference to the graphical representation 306, the user 112 achieved the emotional peak 314 at 7 pm. This type of analysis and representation in emotion intensity levels assists the user 112 to be conscious of their own emotional triggers and emotional peaks in a specific context or a given situation that may be specific to a user, such as the user 112.

In accordance with an embodiment, the emotion recognition and prediction engine 206 may be configured to detect the emotional peak 314 based on the threshold intensity. In accordance with an embodiment, the emotion recognition and prediction engine 206 may be configured to detect the change in the emotional characteristic of the user 112 based on the detected emotional peak 314. In accordance with an embodiment, the emotion recognition and prediction engine 206 may be configured to detect the dominant emotion of the user 112 based on the detected emotional peak 314 of the time period.

Figure 4:
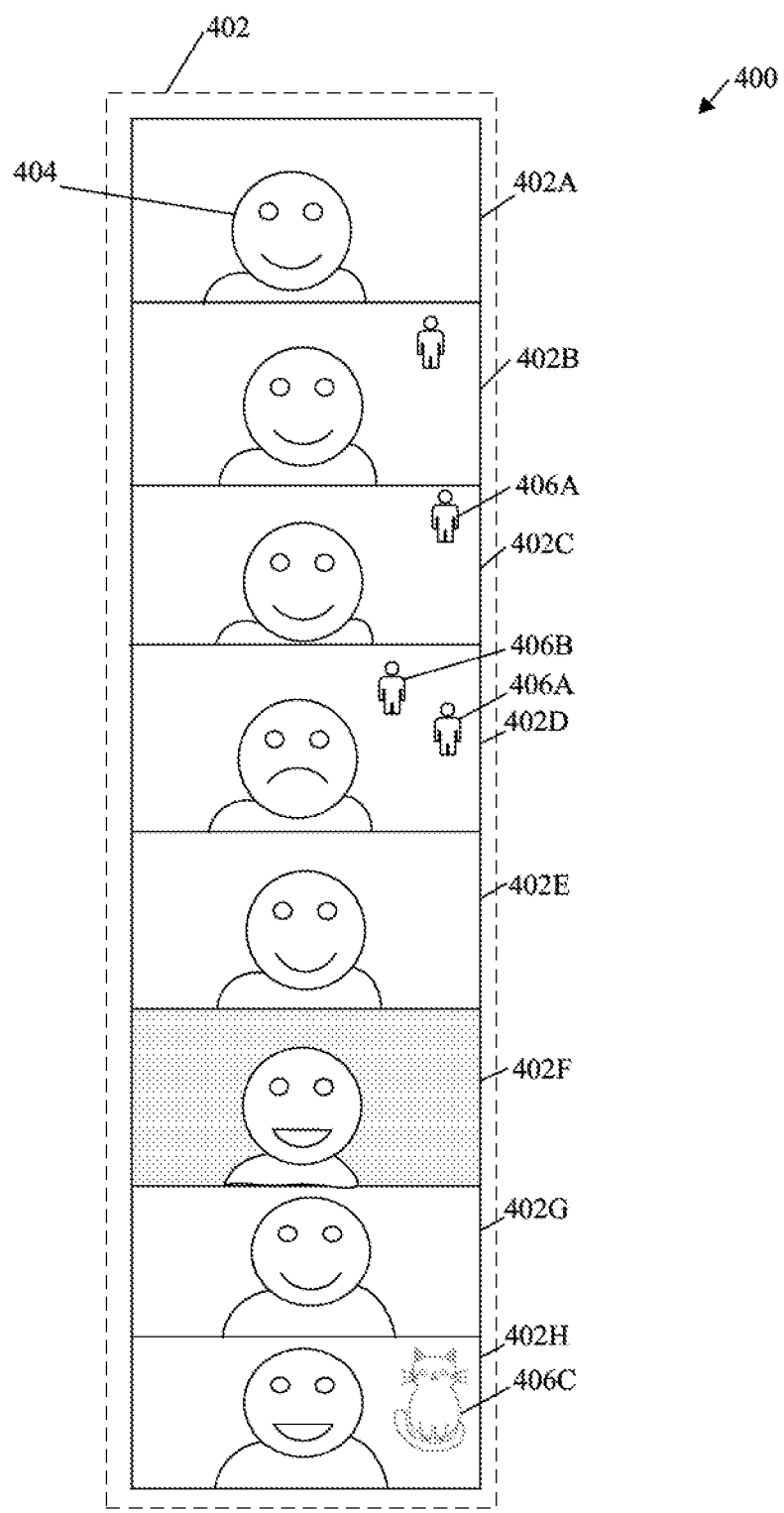
FIG. 4 illustrates exemplary operations to detect triggers in detected dominant emotion, by the electronic apparatus of FIG. 2, in accordance with an embodiment of the disclosure.

FIG. 4 illustrates exemplary operations for detecting triggers in detected dominant emotion, by the electronic apparatus of FIG. 2, in accordance with an embodiment of the disclosure. FIG. 4 is explained in conjunction with elements from FIGS. 1, 2, 3A, and 3B. With reference to FIG. 4, there is shown a plurality of image frames 402 that includes, for example, image frames 402A to 402H captured by the image capturing device 106C over the specified time period. The plurality of image frames 402 in FIG. 4 may be similar to the plurality of image frames 302 in FIG. 3. The image frames 402A to 402H may include user representation 404 (or detected emotion) of the user 112. In some embodiments, the image frames 402A to 402H may also include information related to surroundings of the user 112 during the specified time period of capture of the user information. The information related to the surroundings may include information related events (such as dance party, musical event, birthday celebration, official meeting, or examination hall) occurred near the user 112, second content the user 112 may be viewing or listening or information about another user in proximity to the user 112 (e.g., a family member, a friend, or a pet who may have an influence related to emotion of the user 112). Such information related to the surrounding of the user 112 may change the facial expression (or the emotion characteristic) of the user 112 and may be referred as the triggers related to the user 112. In some embodiments, the triggers related to the user 112 may include information related to environmental conditions near the user 112, date-time information, or the current location of the user 112. In some embodiments, the triggers related to the user 112 may include information related to one or more non-living objects (for example, gifts, pictures, decorative items, or furniture items) around the user 112.

In FIG. 4, a first image frame 402A of the image frames 402A to 402H may include a user representation 404 (the emotion characteristic) of the user 112. A second image frame 402B and a third image frame 402C of the image frames 402A to 402H may include a first person 406A in the surroundings of the user 112. The captured facial expressions (or the emotion characteristic) of the user 112 in the first image frame 402A, the second image frame 402B and the third image frame 402C may be same as happy (or smiling). A fourth image frame 402D of the image frames 402A to 402H may include a second person 406B in the surrounding of the user 112. The fourth image frame 402D may indicate the emotion characteristic of the user 112 as sad emotion. In accordance with an embodiment, the emotion recognition and prediction engine 206 may be configured to detect the second person 406B as the trigger in the fourth image frame 402D which caused the change in the emotional characteristic of the user 112 from the happy emotion to the sad emotion.

A fifth image frame 402E of the image frames 402A to 402H does not include the first person 406A and the second person 406B. In FIG. 4, the detected emotion of the user 112 in the fifth image frame 402E may represent the happy emotion. The emotion recognition and prediction engine 206 may be configured to detect the absence of the first person 406A and the second person 406B in the fifth image frame 402E as the trigger for the positive change (sad to happy) in the emotion characteristic from the fourth image frame 402D to the fifth image frame 402E.

In accordance with an embodiment, other factors related to the triggers (such as the environment conditions, events, location, background lighting) of the user 112 may remain unchanged from the first image frame 402A to the fifth image frame 402E. A sixth image frame 402F of the image frames 402A to 402H may indicate a darker background lighting in the surrounding of the user 112 as compared to other image frames. The emotion recognition and prediction engine 206 may be configured to detect the increase in an intensity level of the happy emotion in the sixth image frame 402F with the change in the background lighting (for example as the environment conditions) around the user 112 from the fifth image frame 402E to the sixth image frame 402F. The emotion recognition and prediction engine 206 may be configured to detect the change in the background lighting as the trigger, which caused the change in the intensity level of the particular emotion (say happy) of the user 112. This may indicate that the user 112 likes the dark background lighting which increased the intensity level of the happiness of the user 112. In a seventh image frame 402G of the consecutive image frames 402A to 402H, with the change in the background lighting (say dark to bright), the emotion recognition and prediction engine 206 may be configured to detect the change in the intensity level of the happy emotion of the user 112. In an eighth image frame 402H of the image frames 402A to 402H may include a pet 406C in the surrounding of the user 112. The emotion recognition and prediction engine 206 may be configured to detect the increase in the intensity level of the happy emotion in the eighth image frame 402H with the presence of the pet 406C (as the trigger) around the user 112 from the seventh image frame 402G to the eighth image frame 402H.

In accordance with an embodiment, the emotion recognition and prediction engine 206 may be configured to detect the event (as the trigger) occurred with the user 112 during the image frames 402A to 402H to detect the change in the emotional characteristic or change in the intensity level. In accordance with an embodiment, the emotion recognition and prediction engine 206 may be configured to detect a current location (as the trigger) of the user 112 to detect the change in the emotional characteristic or change in the intensity level. In accordance with an embodiment, the emotion recognition and prediction engine 206 may be configured to detect the environment condition (as the trigger) in the vicinity of the user 112 to detect the change in the emotional characteristic or change in the intensity levels (dominant emotion). Examples of the environment condition may include, but are not limited to, temperature, rainfall, or humidity. In some embodiments, the emotion recognition and prediction engine 206 may be configured to detect the second content (as the trigger) which the user 112 might be watching or listing or the action which the user 112 might be performing during the capture of the image frames 402A to 402H. Thus, the emotion recognition and prediction engine 206 may be able to correlate the detected trigger in the plurality of image frames 402 (or the user information) with the detected dominant emotion (change in the emotional characteristics or the change in the intensity levels) of the user 112. The electronic apparatus 102 may be configured to recommend the first content or the information related to the action based on the correlation of the detected trigger with the dominant emotion of the user 112. Thus, the emotion recognition and prediction engine 206 may be configured to generate insightful information (e.g., the deductive information) to enable different users to be conscious of their own emotional triggers and emotional peaks in a specific context or a given situation that may be specific to a user, such as the user 112, which may then be used for self-corrective action and improve overall emotional health.

Figure 5A:
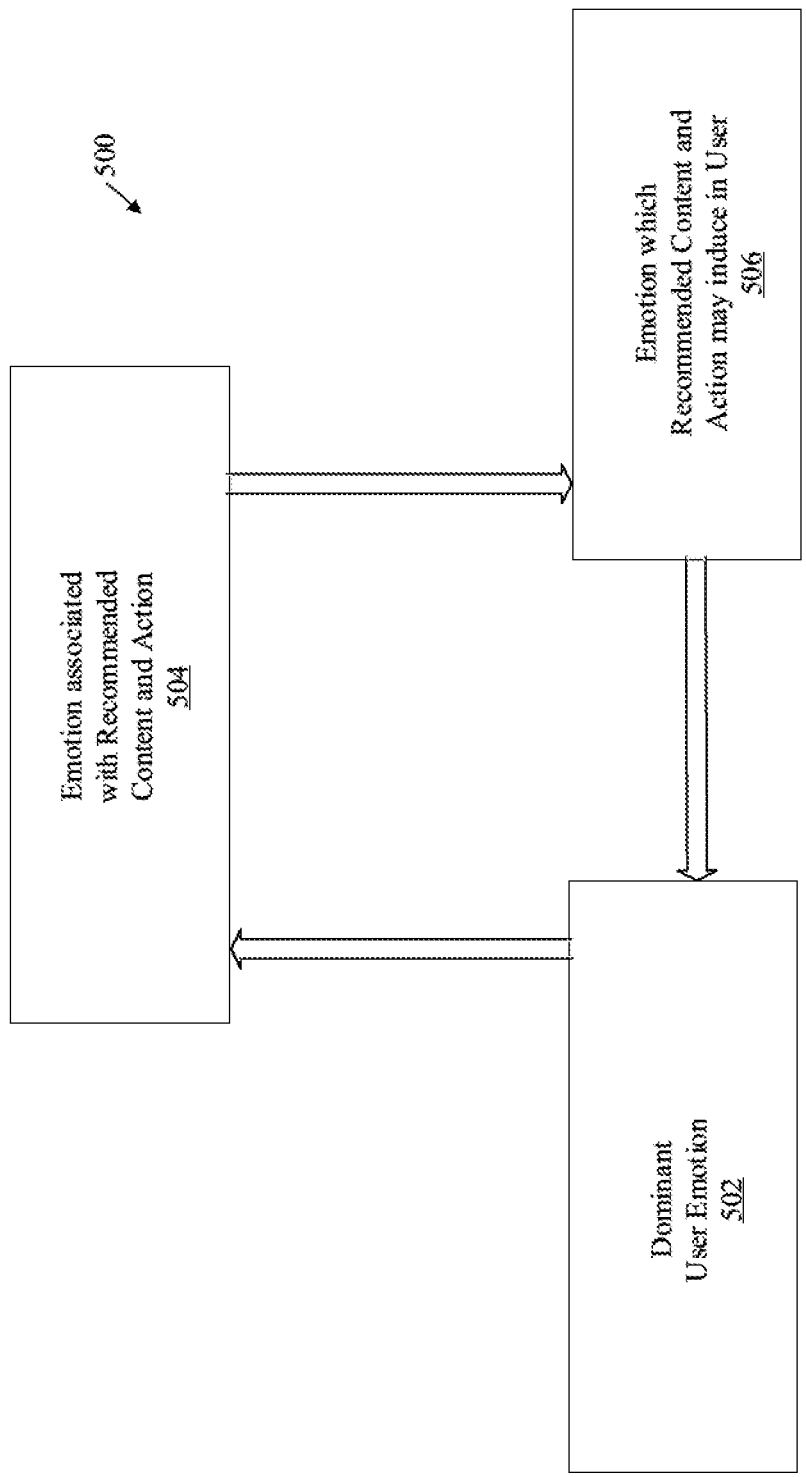
FIGS. 5A and 5B, collectively, illustrates exemplary operations to predict emotions for user, by the electronic apparatus of FIG. 2, in accordance with an embodiment of the disclosure.
Figure 5B:
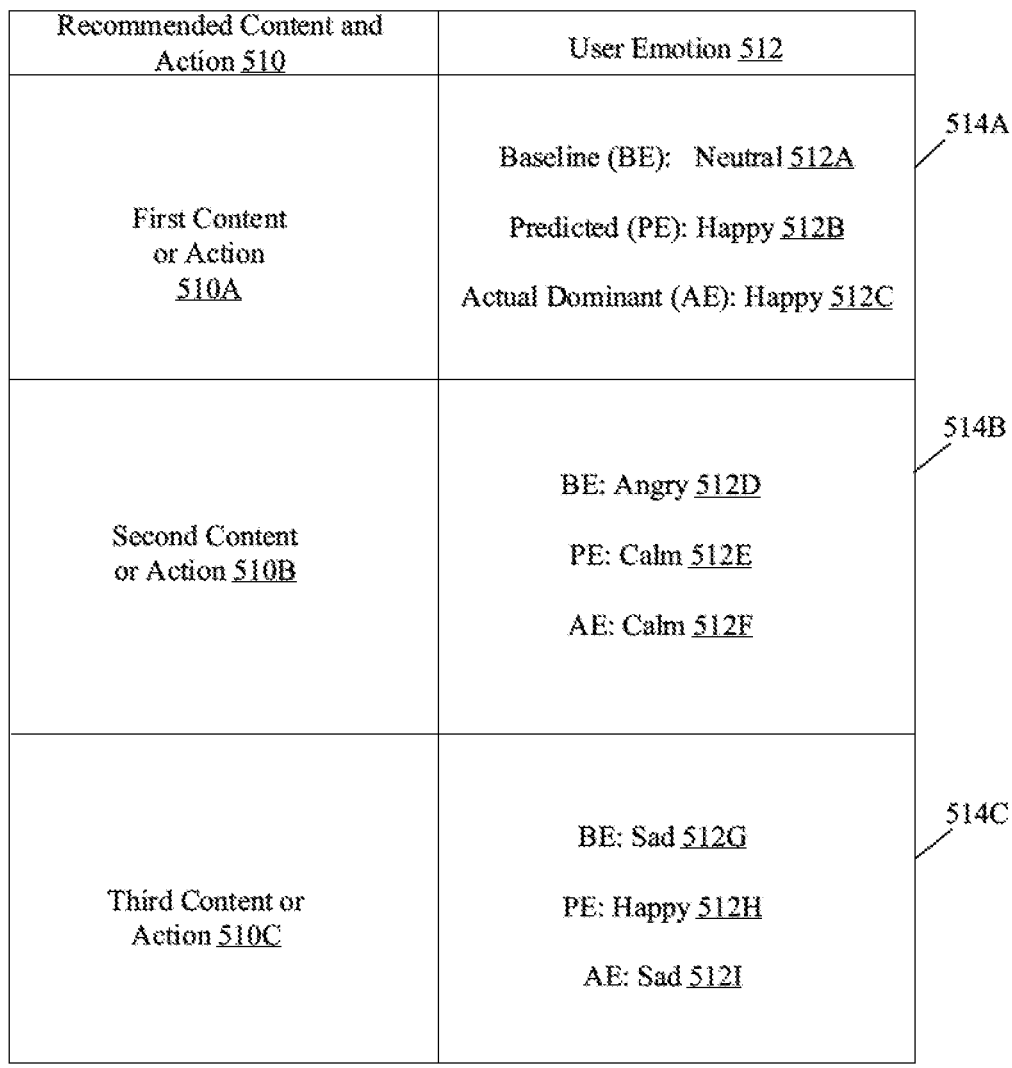

FIGS. 5A and 5B, collectively, illustrates exemplary operations to predict emotions for the user 112, by the electronic apparatus of FIG. 2, in accordance with an embodiment of the disclosure. FIG. 5A are explained in conjunction with elements from FIGS. 1, 2, 3A, 3B, and 4. With reference to FIG. 5A, there is shown a graphical representation 500 to depict an emotional triangle. The graphical representation 500 of the emotional triangle may include a dominant emotion 502, an emotion associated with the recommended content or action 504, and an emotion 506 that the first content or the action may induce in the user 112.

In accordance with an embodiment, the emotion recognition and prediction engine 206 may be configured to detect the dominant emotion 502 of the user 112. The detection of the dominant emotion of the user 112 have been described in detail, for example in FIGS. 3A, 3B and 4. In accordance with an embodiment, the emotion recognition and prediction engine 206 may be further configured to detect the emotion 504 associated with the first content or action output or recommended to the user 112 based on the detected dominant emotion 502. In some embodiments, the emotion recognition and prediction engine 206 may be further configured to retrieve the emotion 504 associated with the first content or action from the server 108 via the communication network 104. The emotion recognition and prediction engine 206 may be further configured to predict the emotion 506 of the user 112 that may be induced in the user 112 based on the recommended content or action. For example, when the detected dominant emotion 502 of the user 112 is the sad emotion, the electronic apparatus 102 may be configured to recommend the first content or action associated with the emotion 504 as the happy emotion. The first content or action with the associated happy emotion 504 may change the emotional characteristic of the user 112 to the positive emotional type (say happy) from the negative emotional type (say sad). Thus, the emotion recognition and prediction engine 206 may be configured to predict the emotion 506 as the happy emotion which may be induced in the user 112 by the recommended first content or action.

In accordance with an embodiment, the predicted emotion 506 (PE) may be based on the user-content preference information and the user past emotional information received from the server 108. The user-content preference information may indicate which type of content (audio, video, image) may be preferred by the user 112 and may induce the positive emotion in the user 112. The user-content preference information may further indicate favorite places of the user 112 or near-by events the user 112 might be interested in. The user-content preference information may include information about a role model (such as celebrity) liked by the user 112. The processor 204 may be configured to identify the first content or action for recommendation based on the information about the role model. The first content or action identified based on the information about the role model may include an image of the role model where the image may indicate the positive behavior or the emotional characteristic (say happy) of the role model. In such case, the first content or action which includes the happy image of the role model may induce the positive emotion in the user 112. In accordance with an embodiment, the processor 204 may recommend an activity-to-do (as the action) to the user 112 based on the behavior or the emotional characteristic of the role model in the first content or action. The recommended activity may assist the user 112 to imitate the behavior of the liked role model. The recommended first content or action based on the information about the role model may assist the user 112 to understand different ways or solutions which helped the role model to improve their emotional quotient in different situations.

In accordance with an embodiment, the past user emotional information may correspond to the user's past history with respect to the recommended first content or action and induced emotion in the user 112. The user past emotional information may include internet browsing history of the user 112 and frequency of viewing/listening different content by the user 112. The content with high frequency may indicate a highly preferred content by the user 112 under a given situation/emotion and may induce the positive emotion in the user 112.

In accordance with an embodiment, the emotion recognition and prediction engine 206 may be configured to detect an actual dominant emotion (AE) that was induced in the user 112 in response to the recommended first content or action. The processor 204 may be further configured to update the user-content preference information and the user past emotional information based on the detected AE of the user 112 in response to the recommended first content or action for future predictions. The processor 204 may be further configured to send the updated user-content preference information and the user past emotional information to the server 108. Thus, the electronic apparatus 102 may accurately perform a detailed emotional analysis, prediction, and recommendation of content or action to the user 112. Further, the emotional storyboard generated based on the detailed emotional analysis may facilitate the user 112 with the detailed awareness about their emotional health and further motivate the user 112 to take necessary actions for the improvement of their emotional quotient. Thus, the present disclosure may provide several advantages over conventional systems.

With reference to FIG. 5B, there is shown a graphical representation 508 of a user emotion 512 for different recommended content 510 to the user 112. In the graphical representation 508, for the first content or action 510A, the detected baseline emotion (BE) 512A before the recommendation of the first content or action 510A may be a neutral emotion. The emotion recognition and prediction engine 206 may be configured to predict that the first content or action 510A may make the user 112 happy. The emotion recognition and prediction engine 206 may be configured to determine the predicted emotion (PE) 512B based on the user-content preference information and the user past emotional information. The processor 204 may be configured to detect the actual dominant emotion (AE) 512C as the happy emotion that was induced in the user 112 in response to the recommended first content or action 510A. Further, in FIG. 5B, for the second content or action 510B, the baseline emotion (BE) 512D of the user 112 may be an angry emotion, the predicted emotion (PE) 512E may be a calm emotion, and the actual dominant emotion (AE) 512F may be the calm emotion that was induced in the user 112 in response to the second content or action 510B. Further, in FIG. 5B, for the third content or action 510C, the baseline emotion (BE) 512G of the user 112 may be an sad emotion, the predicted emotion (PE) 512H may be a happy emotion, and the actual dominant emotion (AE) 512I may be the sad emotion that was induced in the user 112 in response to the third content or action 510C. The emotion recognition and prediction engine 206 may be configured to detect a difference in the predicted emotion (PE) 512H and the actual dominant emotion (AE) 512I for the third content or action 510C and update the user-content preference information and the user past emotional information of the user 112 for future recommendation and prediction. Therefore, the electronic apparatus 102 may be able to recommend appropriate content or action to the user 112 to suitably convert the emotional quotient of the user 112 from the negative emotional type to the positive emotional type (for example sad to happy with the first content or action and angry to calm with the second content or action in FIG. 5B).

Figure 6:
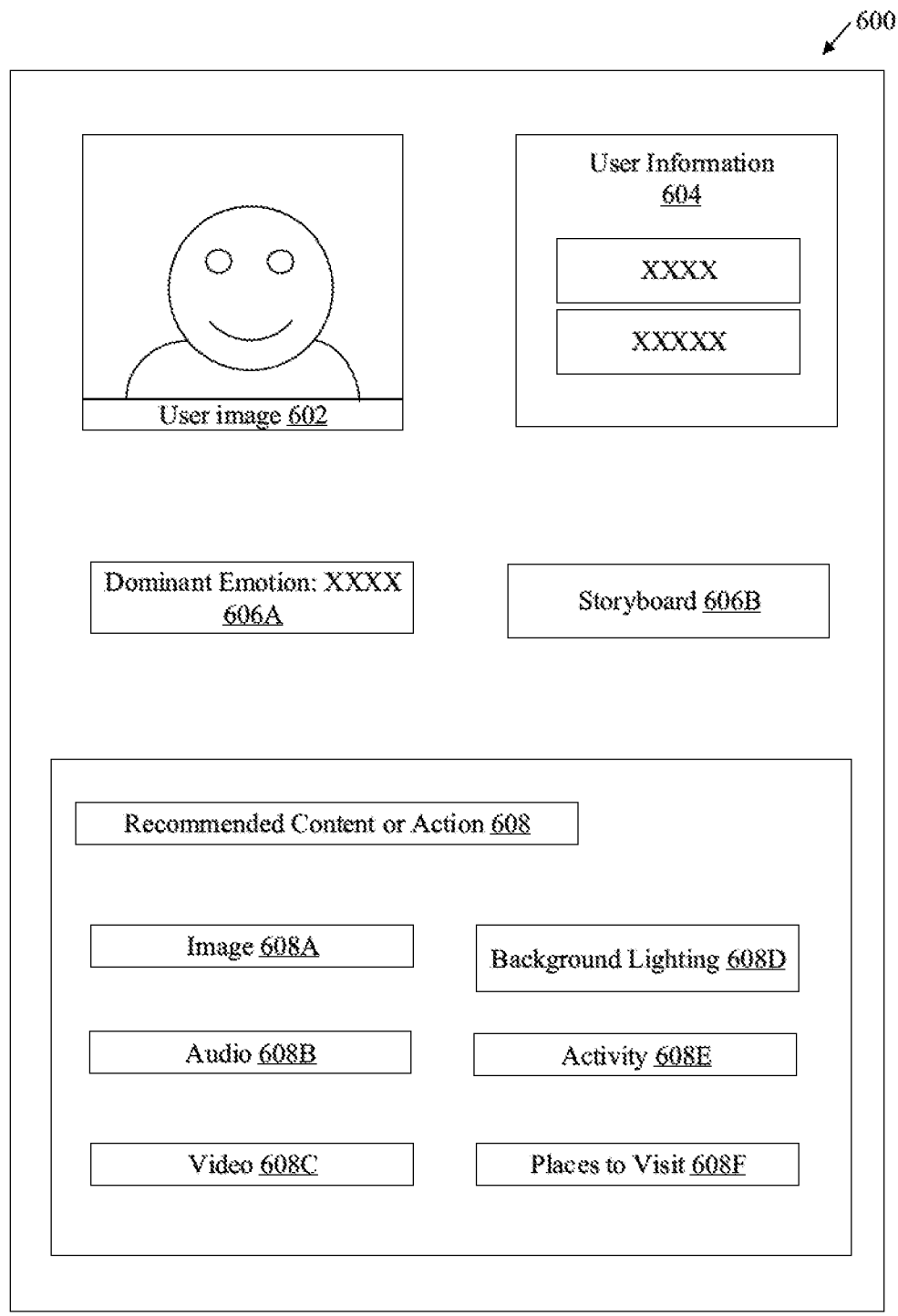
FIG. 6 illustrates an exemplary first user interface to display recommended content or action, in accordance with an embodiment of the disclosure.

FIG. 6 illustrates an exemplary first user interface to display recommended content or action, in accordance with an embodiment of the disclosure. FIG. 6 is explained in conjunction with elements from FIGS. 1, 2, 3A, 3B, 4, 5A and 5B. With reference to FIG. 6, there is shown an exemplary first user interface (UI) 600 which may be rendered on the display device 214A. The first UI 600 includes a user image area 602, user information area 604, and a dominant emotion area 606A of the user 112. There is also shown an emotional storyboard UI element 606B, and a recommendation content or action UI element 608. The recommendation content or action UI element 608 may include an image UI element 608A, an audio UI element 608B, a video UI element 608C, a background lighting UI element 608D, an activity UI element 608E, and places to visit UI element 608F.

The processor 204 may be configured to display an image of the user 112 (captured at the time of registration) on the user image area 602. In accordance with an embodiment, the processor 204 may be configured to display the captured user information (e.g., different emotions) of the user 112 on the user information area 604. The display user information may include, but are not limited to, the biometric data, height, weight, breathing intensity, or body temperature of the user 112.

The processor 204 may be configured to display the detected dominant emotion of the user 112 at the dominant emotion area 606A. For example, the dominant emotion area 606A may display the sad emotion in case the emotion recognition and prediction engine 206 detects the emotional characteristics of the user 112 as the sad emotion. The processor 204 may be configured to receive a user input to display the generated emotional storyboard through the emotional storyboard UI element 606B. For example, the user 112 may select the emotional storyboard UI element 606B to display the emotional storyboard on the user 112 on the display device 214A. A graphical representation of the generated emotional storyboard is described in detail, for example in FIGS. 7A to 7C.

In accordance with an embodiment, the processor 204 may be configured to receive a user input as a preference for content type of the recommended first content or action from the user 112. The user 112 may provide the user input as the preference for the content type through one of the image UI element 608A, the audio UI element 608B, the video UI element 608C, the background lighting UI element 608D, the activity UI element 608E, or the places to visit UI element 608F. For example, if the user 112 wishes to view a movie, the user 112 may select the video UI element 608C of the recommendation content or action UI element 608. The processor 204 may be configured to recommend the first content as video content (say a specific movie) based on the selection of the video UI element 608C by the user 112. Similarly, the processor 204 may be configured to control the background lighting around the user 112 based on the selection of the background lighting UI element 608D by the user 112.

In accordance with an embodiment, the processor 204 may be configured to transmit a signal to an external device based on the negative emotional type of the dominant emotion (for example sad, angry). The processor 204 may be further configured to transmit a warning notification, as the signal, to the external device. In accordance with an embodiment, the external device may be related to other people (for example parents, guardians, friends) who are in relation with the user 112.

In accordance with an embodiment, the processor 204 may be configured to detect the location of the user 112 using the GPS. The processor 204 may be further configured to output information that recommends an activity-to-do or information about a place-to-visit (as the action) to the user 112 based on the detected location. In accordance with an embodiment, the processor 204 may be configured to detect health status information of the user 112 based on the user information captured by the plurality of sensors 106. The health status information may indicate a health-related issue (for example as high blood pressure, fever) with the user 112. The processor 204 may be further configured to recommend the first content or action to the user 112 to resolve the health-related issue based on the detect health status information. In such case, the first content or action may indicate information about medicines or diagnostic centers or hospitals to the user 112.

In accordance with an embodiment, the processor 204 may be configured to recommend the first content or action based on the user-content preference information, the user past emotional information received from the server 108, the detected triggers which caused the change in the emotional characteristics, and the user input (as the preference for the content type) received from the user 112 through the first UI 600. Thus, depending on the various aforementioned factors, the electronic apparatus 102 may accurately recommend the first content or action to the user 112 which may further ensure the improvement in the emotion health of the user 112 effectively. In accordance with an embodiment, the processor 204 may be configured to recommend the first content or action as a notification to the user 112 on the I/O device 214A. The notification may be an image, an audio sound, a haptic output such as a vibration. In some embodiments, the first UI 600 may be displayed at an external apparatus or an external application, via an application programming interface (API) for content or action recommendation.

Figure 7B:
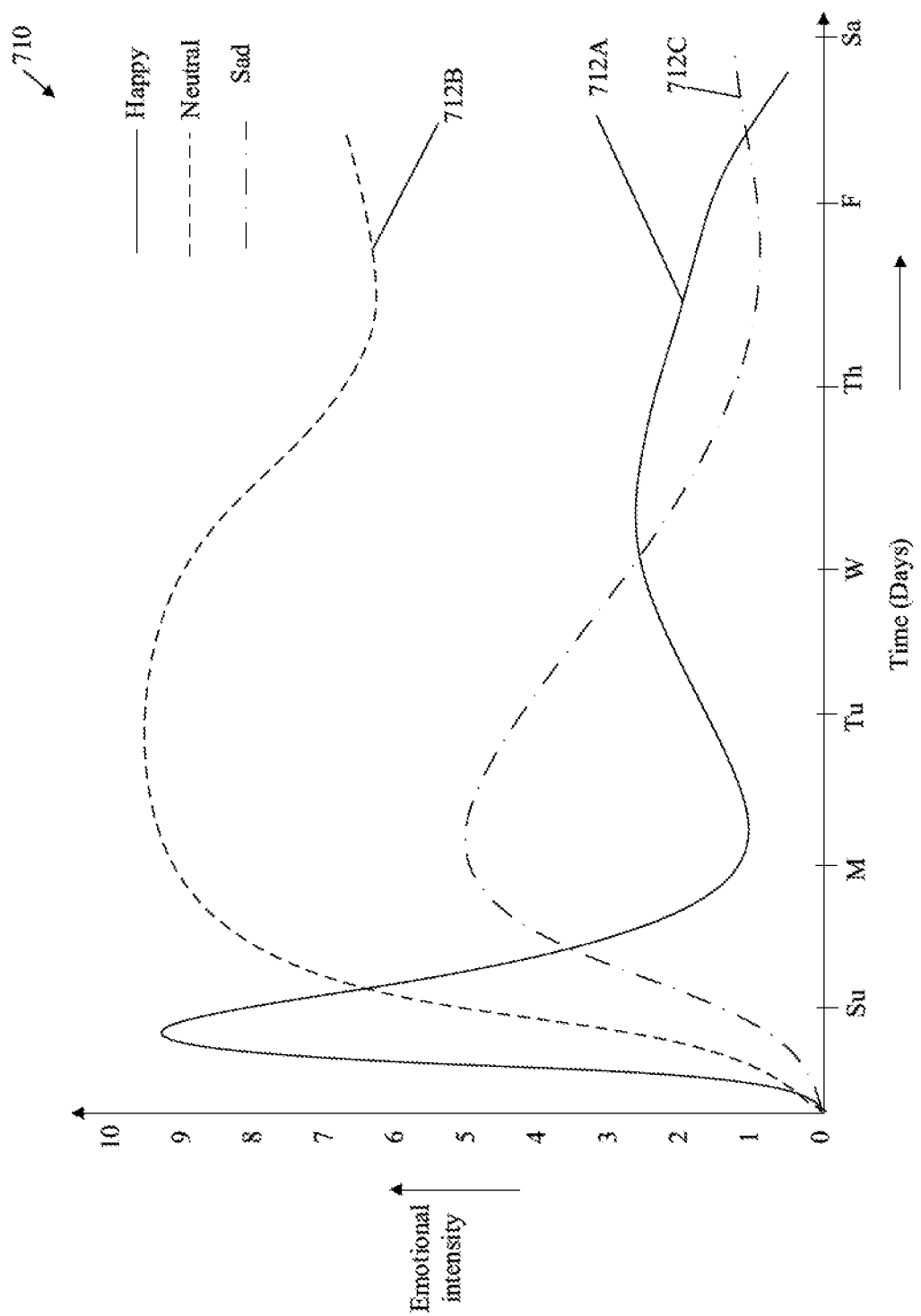
Figure 7C:
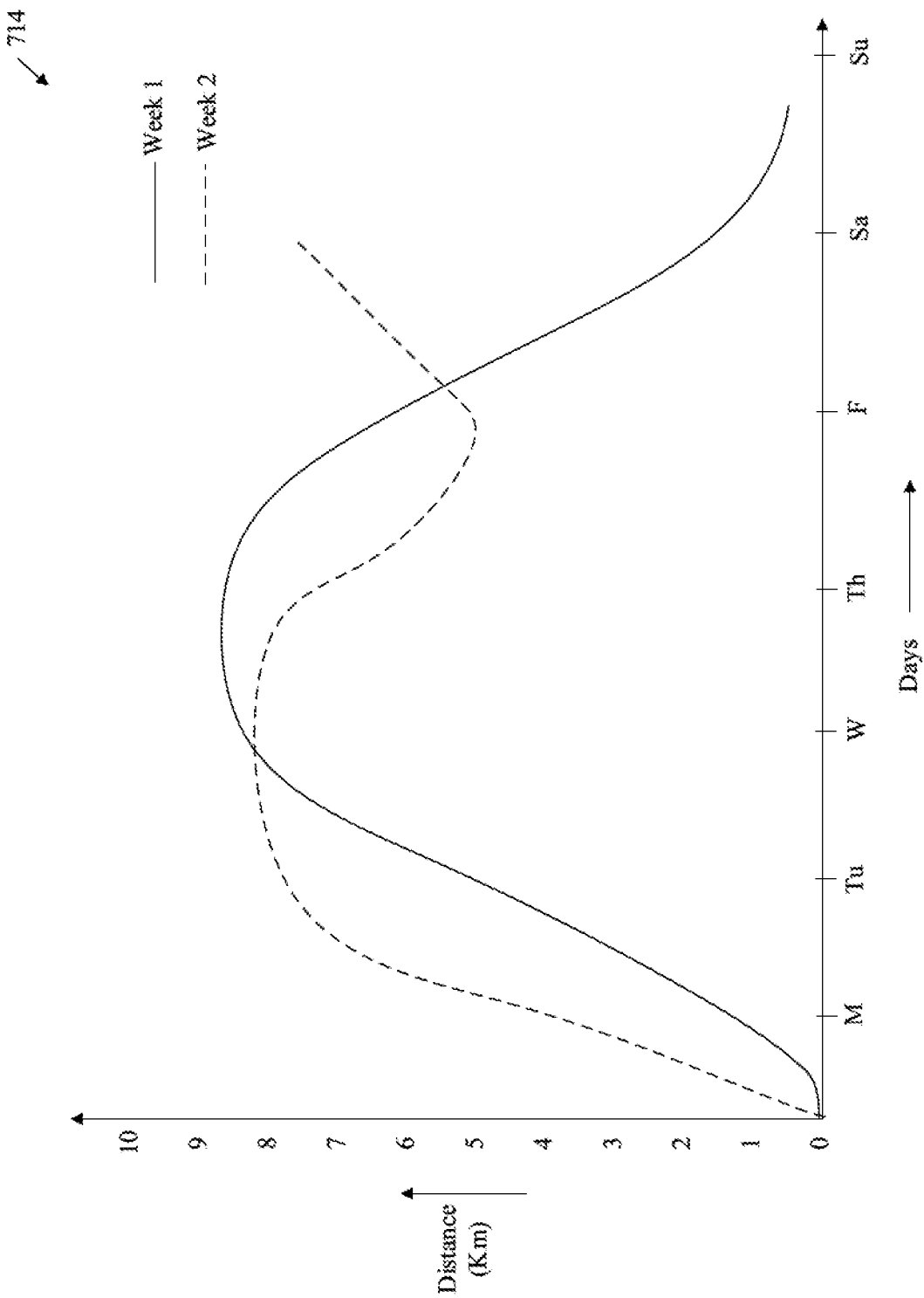

FIGS. 7A, 7B, and 7C, collectively, illustrate exemplary second user interface to display an emotional storyboard, in accordance with an embodiment of the disclosure. FIGS. 7A, 7B, and 7C are explained in conjunction with elements from FIGS. 1, 2, 3A, 3B, 4, 5A, 5B, and 6. With reference to FIG. 7A, there is shown a first emotional storyboard 700 of the second user interface rendered on the display device 214A. In accordance with an embodiment, the processor 204 may be configured to communicate the generated emotional storyboard to an external display device. The first emotional storyboard 700 of the second user interface may include time stamp information 702, trigger information 704, user emotion information 706, and other user information, such as user information 708.

In accordance with an embodiment, the emotional storyboard generator 208 may be configured to generate the first emotional storyboard 700. The time stamp information 702 may indicate the specified time period over which the user emotion information 706 was captured from the plurality of sensors 106. The first emotional storyboard 700 may further include the trigger information 704 that corresponds to different triggers which caused the change in the emotional characteristic of the user 112. Examples of the triggers are described in detail, for example, in FIG. 4. The first emotional storyboard 700 may display different triggers for different time stamps in the time stamp information 702.

The first emotional storyboard 700 may further include the user emotion information 706. The user emotion information 706 may indicate different emotions of the user 112 in different time stamps and with the associated triggers. The first emotional storyboard 700 may further include the user information 708 received from the plurality of sensors 106. The user information 708 may indicate the physiological and non-physiological features (such as body temperature, blood pressure, heartbeat, etc) of the user 112 received from the plurality of sensors 106 during different time period indicated by the time stamp information 702. In accordance with an embodiment, the first emotional storyboard 700 may include the user emotions for different time period such as for an hour, a day, a week, or a year.

In accordance with an embodiment, the first emotional storyboard 700 may further include the baseline emotion and the dominant emotion detected by the emotion recognition and prediction engine 206 over the specified time period indicated by the time stamp information 702. The first emotional storyboard 700 may further include an indicator (for example icon, weblink) that corresponds to the first content recommended to the user 112 during the specified time period. In accordance with an embodiment, the emotional storyboard may further include the change in the dominant emotion based on the recommended first content or action to the user 112.

In accordance with an embodiment, the first emotional storyboard 700 may further include an avatar of the user 112. The avatar may indicate virtual emotions (such as a smile for happiness and tears for sadness) in the emotional storyboard. The virtual emotions may correspond to the emotions of the user 112 in response to the trigger information 704 at different time period specified in the time stamp information 702.

With reference to FIG. 7B, there is shown a second emotional storyboard 710 in the second user interface. The second emotional storyboard 710 may indicate, for example, a day-wise distribution of various emotions of the user 112 for a particular time period (say of one week). In some embodiments, second emotional storyboard 710 may indicate, but is not limited to, a month-wise or year-wise distribution of various emotions of the user 112 based on the user input received from the user 112. In FIG. 7B, the second emotional storyboard 710 may indicate the day-wise distribution of, but is not limited to, a happy emotion 712A, a neutral emotion 712B, and a sad emotion 712C to the user 112. In some embodiments, the second emotional storyboard 710 may indicate the day-wise distribution of other plurality of categories of user emotions as described, for example, in FIG. 1. The second emotional storyboard 710 may include the emotional intensity for each day of the week when the user 112 had a specified emotion (such as the happy emotion 712A, the neutral emotion 712B, and the sad emotion 712C). Such detailed representation in the second emotional storyboard 710 may provide the user 112 a comprehensive view of the user's emotional health for the specified time period. With reference to FIG. 7B, for example on Sunday (Su), the user 112 may be happy with an emotional intensity of a higher level (for example "9"), neutral with the emotional intensity of a medium level (for example "5") and sad with the emotional intensity of a lower level (for example "1"). In another example, on Monday (M) the user 112 may be happy with the emotional intensity of the lower level (for example "1"), neutral with the emotional intensity of the high level (for example "9") and sad with the emotional intensity of the medium level (for example "5"). Similarly, the FIG. 7B shows that the emotional characteristic and intensity of the user 112 for rest of the week including Tuesday (Tu) Wednesday (W) Thursday (Th) Friday (F), and Saturday (Sa). In accordance with an embodiment, the electronic apparatus 102 may be configured to alter a number of category of emotions and the specified time period in the second emotional storyboard 710 based on the user input received from the user 112. In accordance with an embodiment, the emotional storyboard generator 208 may be configured to generate a storyboard similar to the second emotional storyboard 710 that may display other variants of emotions of the user 112, such as anger, disgust, excitement, sorrow, fear, etc.

With reference to FIG. 7C, there is shown a third emotional storyboard 714 in the second user interface. The third emotional storyboard 714 may include a graphical representation of a physical activity index of the user 112 for the specified time period (say for two weeks). In accordance with an embodiment, the emotional storyboard generator 208 may be configured to generate the third emotional storyboard 714 to indicate the physical activity index of the user 112 based on physical movement of the user 112 and the user information received from the plurality of sensors 106. In accordance with an embodiment, the emotional storyboard generator 208 may be configured to detect the duration of a physical activity and a sleep cycle of the user 112 over the specified time period to calculate the physical activity index of the user 112.

The third emotional storyboard 714 may indicate a comparison of two physical activity index for different time period. A solid line may represent a first physical activity index for a first week and a dotted line may represent a second physical activity index for a second week. In FIG. 7C, on Monday (M), Tuesday (Tu), and Saturday (Sa) the second physical activity index of the user 112 is more than the first physical activity index. However, on Thursday (Th), and Friday (F) the first physical activity index of the user 112 was more than the physical positive activity index. Thus, the third emotional storyboard 714, in FIG. 7C, may assist the user 112 to analyze differences in the physical activities for each week and take appropriate action to improve the physical activity index and the emotional quotient. In accordance with an embodiment, the emotional storyboard generator 208 may be configured to generate a storyboard similar to the third emotional storyboard 714 that may display calories burnt or time spent on physical activity by the user 112 during the first week and the second week. In some embodiments, the first emotional storyboard 700, the second emotional storyboard 710, and the third emotional storyboard 714 may be displayed at an external apparatus or an external application, via an application programming interface (API) for content recommendation.

In accordance with an embodiment, the emotional storyboard generator 208 may be further configured to set a timing goal of the physical activity and the sleep cycle for the user 112 to be achieved each day based on the user information received from the plurality of sensors 106. For example, if the user information of the user 112 indicates that the user 112 is overweight, the emotional storyboard generator 208 may set the timing goal as 2 hours of running for each day to promote user's health and well-being.

Figure 8:
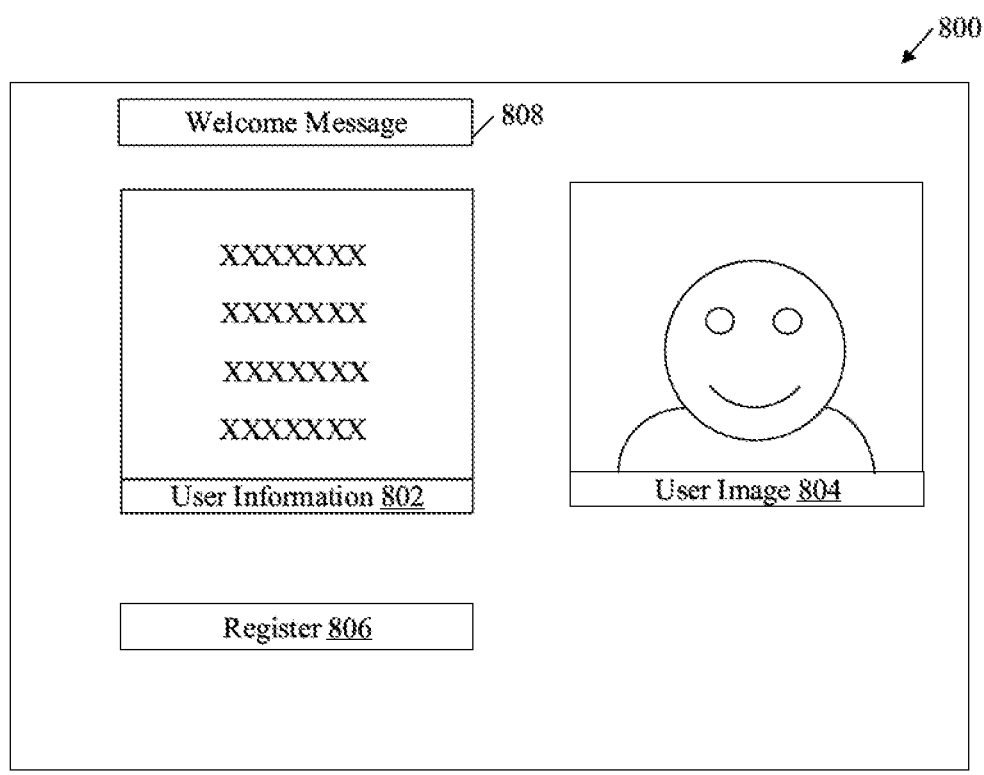
FIG. 8 illustrates exemplary third user interface to display a registration process of a user, in accordance with an embodiment of the disclosure.

FIG. 8 illustrates an exemplary third user interface to display a registration process of a user, in accordance with an embodiment of the disclosure. FIG. 8 is explained in conjunction with elements from FIGS. 1, 2, 3A 3B, 4, 5A, 5B, 6, and 7A to 7C. With reference to FIG. 8, there is shown a third user interface 800. The third user interface 800 may be displayed on the display device 214A to register a new user with the electronic apparatus 102. The third user interface 800 may further include a user information input UI element 802, a user image input UI element 804, a register UI element 806, and a welcome message 808.

In operation, the user 112, may utilize I/O device 214, to provide user related details to the electronic apparatus 102 through the user information input UI element 802 and the user image input UI element 804. For example, the user 112 may provide different information such as name, contact, age, and the like through the user information input UI element 802. Further, the user 112 may click or select the user image input UI element 804 to upload an image stored in the memory 212. The user 112 may also select click or select the user image input UI element 804 to click a real-time image of the user 112 using the image capturing device 106C. The user 112 may initiate the registration with the electronic apparatus 102 through the selection of the register UI element 806. The electronic apparatus 102 may be configured to connect to a social media account of the user 112 for the registration based on the selection of the register UI element 806 by the user 112. In accordance with an embodiment, the electronic apparatus 102 may be configured to initiate the capture of the user information of the user 112 (through the plurality of sensors 106) based on successful completion of the registration between the user 112 and the electronic apparatus 102.

Figure 9A:
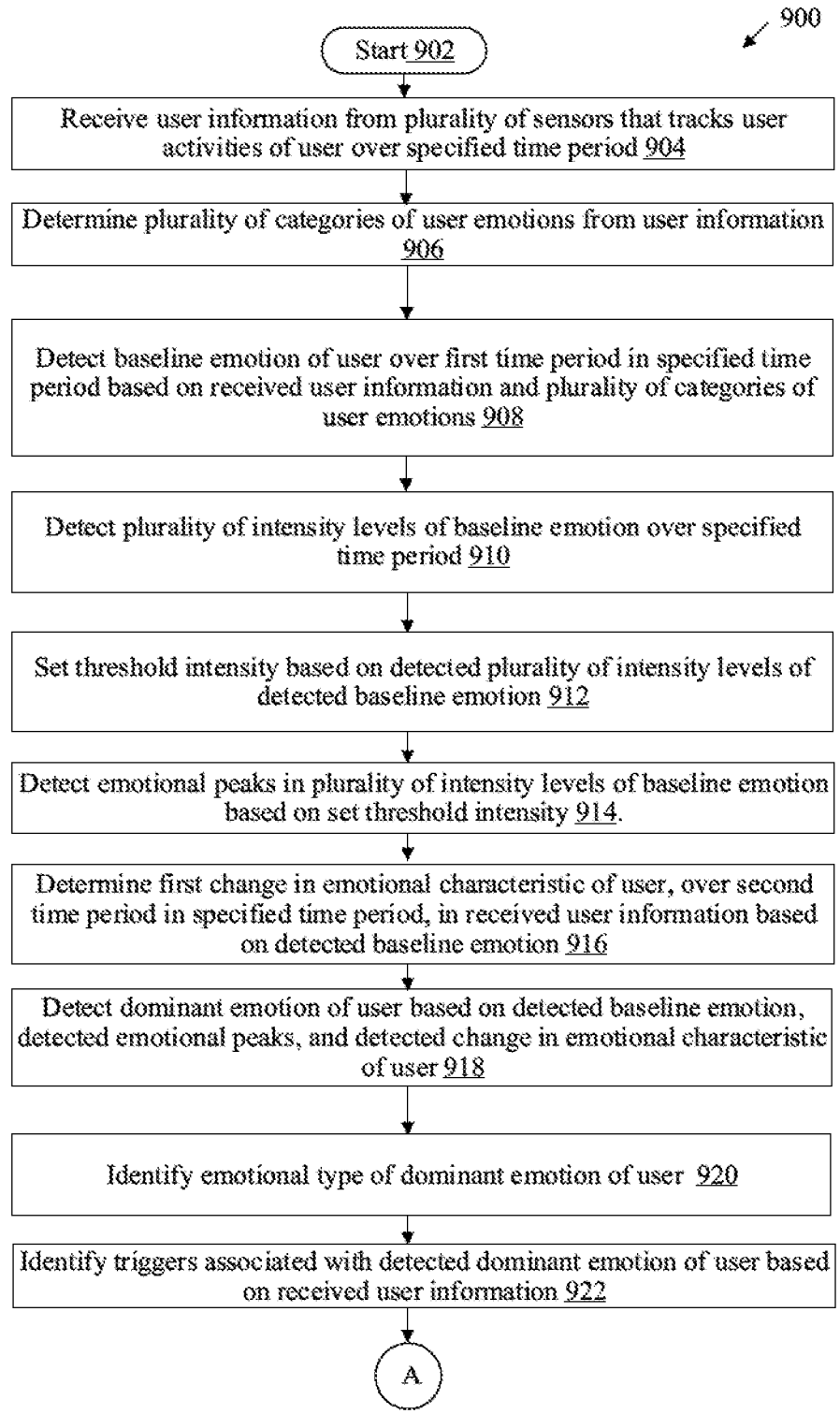
FIGS. 9A and 9B collectively depict a flowchart that illustrates exemplary operations for generating an emotional storyboard and recommending content or action, in accordance with an embodiment of the disclosure.
Figure 9B:
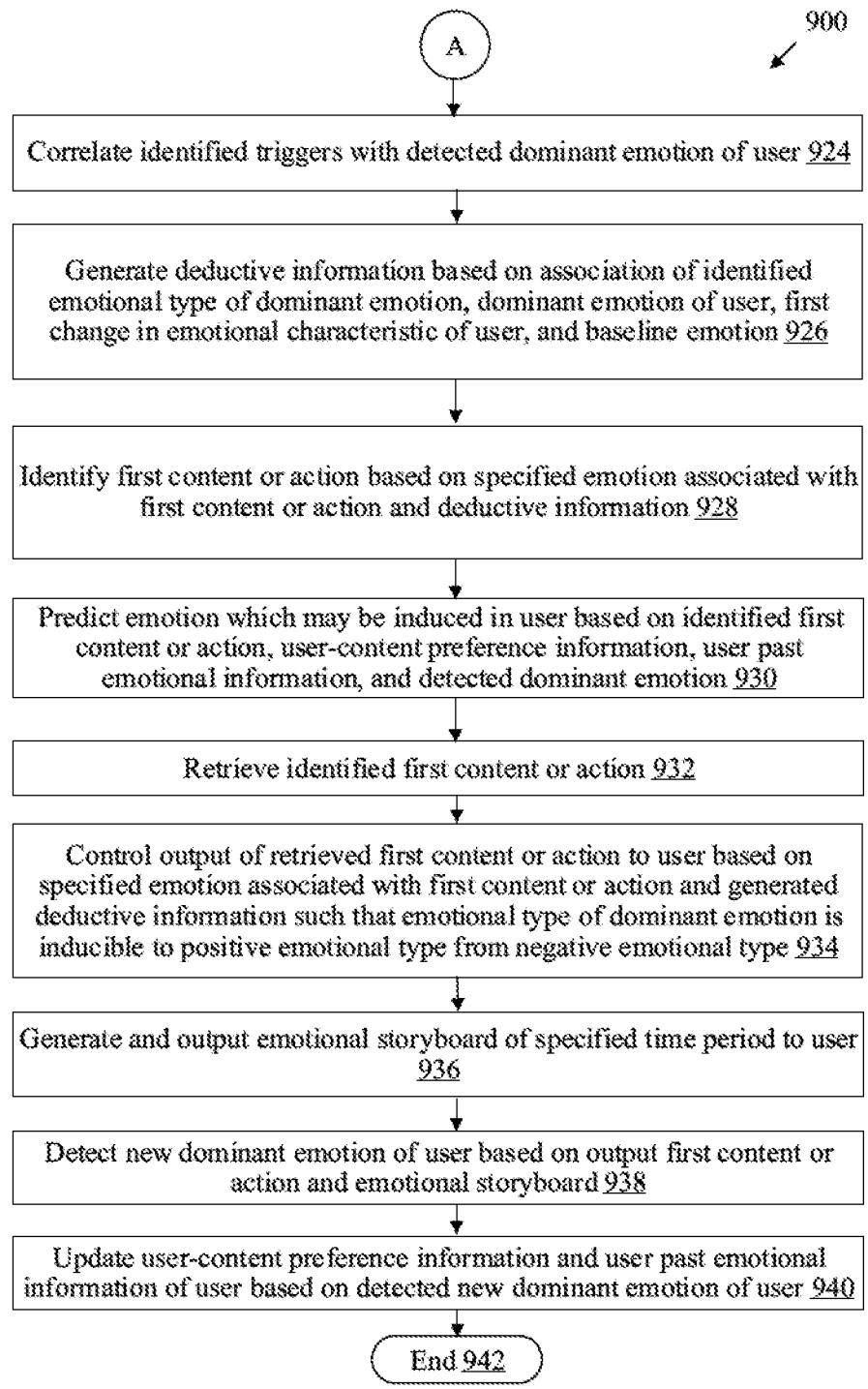

FIGS. 9A and 9B collectively depict a flowchart that illustrates exemplary operations generating an emotional storyboard and recommending content or action, in accordance with an embodiment of the disclosure. With reference to FIGS. 9A and 9B, there is shown a flowchart 9. The flowchart 900 is described in conjunction with FIGS. 1, 2, 3A, 3B, 4, 5A, 5B, 6, 7A to 7C, and 8. The operations from 902 to 940 may be implemented in the electronic apparatus 102. The operations of the flowchart 900 may start at 902 and proceed to 904.

At 904, the user information may be received from the plurality of sensors 106 that tracks user activities of the user 112 over the specified time period. The processor 204 may be configured to receive the user information from the plurality of sensors 106. Examples of the user information may include, but are not limited to, the physiological and non-physiological data of the user 112 such as images, biometric data, location, height, weight, heartbeat, eye gaze, facial expression, blood-flow data, breathing intensity, body temperature, voice tone, voice volume, or head movement. The processor 204 may be further configured to store the user information in the memory 212 of the electronic apparatus 102.

At 906, a plurality of categories of user emotions may be determined from the received user information. In accordance with an embodiment, the processor 204 may be configured to determine a plurality of different categories of user emotions. Each category of user emotion of the plurality of categories of user emotions may correspond to one of a positive emotional type (such as happy) or a negative emotional type (such as sad).

At 908, the baseline emotion of the user 112 may be detected over a first time period in the specified time period based on the received user information and the plurality of categories of user emotions. In accordance with an embodiment, the emotion recognition and prediction engine 206 may be configured to detect the baseline emotion of the user 112 based on the received user information and the plurality of categories of user emotions. The baseline emotion may be an initial baseline emotion which may correspond to a neutral emotion of the user 112. The neutral emotion may be further updated by the electronic apparatus 102 over the first time period to obtain the actual baseline emotion of the user 112.

At 910, a plurality of intensity levels of the baseline emotion may be detected for over the specified time period. The emotion recognition and prediction engine 206 may be configured to detect the plurality of intensity levels of the baseline emotion based on the user information and the received plurality of categories of user emotions (which also includes different values of biometric or voice data for each category).

At 912, a threshold intensity may be set based on the detected plurality of intensity levels of the detected baseline emotion. In accordance with an embodiment, the emotion recognition and prediction engine 206 may be configured to dynamically set the threshold intensity based on the detected plurality of intensity levels.

At 914, emotional peaks in the plurality of intensity levels of the baseline emotion may be detected based on the set threshold intensity. In accordance with an embodiment, the emotion recognition and prediction engine 206 may be configured to detect the emotional peaks of the plurality of intensity levels based on the set threshold intensity. Detection of the emotional peak from the plurality of intensity levels of the baseline emotion may be described in detail, for example in FIG. 3B.

At 916, a first change in the emotional characteristic of the user 112 may be determined over a second time period in the specified time period in the user information based on the detected baseline emotion. The emotion recognition and prediction engine 206 may be configured to determine the change in the emotional characteristic of the user 112 in the user information based on the detected baseline emotion. Determination of the change in the emotional characteristic of the user 112 may be described in detail, for example in FIGS. 3A and 4.

At 918, the dominant emotion of the user 112 may be detected based on the detected baseline emotion, the detected emotional peaks, and the detected change in the emotional characteristic of the user 112. In accordance with an embodiment, the emotion recognition and prediction engine 206 may be configured to detect the dominant emotion based on the detected baseline emotion, the detected emotional peaks, and the detected change in the emotional characteristic. Detection of the dominant emotion of the user 112 may be described in detail, for example in FIGS. 3A, 3B, and 4.

At 920, an emotional type of the dominant emotion of the user 112 may be identified. The emotional type may be one of a positive emotional type or a negative emotional type. In accordance with an embodiment, the dominant emotion may impact and may be used to calibrate the baseline emotion of the user 112.

At 922, triggers associated with the detected dominant emotion of the user 112 may be identified based on the user information. The emotion recognition and prediction engine 206 may be configured to identify triggers associated with the detected dominant emotion of the user 112 based on the user information. Examples of triggers associated with the detected dominant emotion are described in detail, for example, in FIG. 4.

At 924, the identified triggers may be correlated with the detected dominant emotion of the user 112. The emotion recognition and prediction engine 206 may be configured to correlate the identified triggers with the detected dominant emotion (detected change in the emotional characteristic of the user 112 or detected emotional peaks). Examples of the correlation between the triggers and the detected dominant emotion of the user 112 are described in detail, for example, in FIG. 4.

At 926, deductive information may be generated based on an association of the identified emotional type of the dominant emotion, the determined dominant emotion of the first user, the first change in the emotional characteristic of the first user, and the detected baseline emotion. The deductive information may also indicate the correlation between the detected triggers and the detected dominant emotion.

At 928, the first content or action may be identified based on a specified emotion associated with the first content or action and the deductive information. In accordance with an embodiment, the emotion recognition and prediction engine 206 may be configured to identify the first content or action for the user 112.

At 930, an emotion which may be induced in the user 112 may be predicted based on the identified first content or action, the user-content preference information, the user past emotional information, and the detected dominant emotion of the user 112. In accordance with an embodiment, the emotion recognition and prediction engine 206 may be configured to predict the emotion which may be induced in the user 112 based on the identified first content or action, the user-content preference information, the user past emotional information of the user 112, and the dominant emotion as described in detail, for example in FIGS. 5A and 5B.

At 932, the identified first content or action may be retrieved. In accordance with an embodiment, the processor may be configured to retrieve the identified first content or the information related to the action from the multimedia content source 110 via the communication network 104. The processor 204 may be configured to transmit the request for content to the multimedia content source 110 and receive the first content or the information related to the action based on the transmitted request for content. Examples of the first content may include, but are not limited to, audio content, video content, image content, animated content, multimedia content. Examples of the action may include, but are not limited to, information about an activity-do-to, or place-to-visit.

At 934, output of the retrieved first content or action to the user 112 may be controlled at least based on a specified emotion associated with the first content or action and the generated deductive information such that the emotional type of the dominant emotion is inducible to the positive emotional type from the negative emotional type. In accordance with an embodiment, the processor 204 may be configured output the retrieved first content or the information related to the action on the display device 214A for the user 112 or via an audio output device. In some embodiments, the processor 204 may be configured to send the retrieved first content or action to the external device to render the first content or action to the user 112.

At 936, the emotional storyboard for the specified time period may be generated and output to the user 112. In accordance with an embodiment, the emotional storyboard generator 208 may be configured to generate and output a detailed emotional storyboard for the specified time period to the user 112. The emotional storyboard may be described in detail, for example in FIGS. 7A to 7C.

At 938, a new dominant emotion of the user 112 may be detected based on the output first content or action and the emotional storyboard. In accordance with an embodiment, the emotion recognition and prediction engine 206 may be configured to detect the new dominant emotion of the user 112 in response to the output first content or action and the emotional storyboard. The new dominant emotion may be the emotion induced by the recommended content or action, which may be used for future prediction of emotions. The new dominant emotion may be correlated to the AE, which may then be used to accurately determine the content or action to be recommended.

At 940, the user-content preference information and the user past emotional information of the user 112 may be updated based on the detected new dominant emotion of the user 112. The processor 204 may be configured to update the user-content preference information and the user past emotional information in the server 108 based on the captured new dominant emotion captured in response to the recommended first content or action. The control passes to end 942.

Various embodiments of the present disclosure may be found in a method and an electronic apparatus (such as, the electronic apparatus 102) which includes a memory (such as, the memory 212) and circuitry (e.g., the circuitry 202). The memory may be configured to store user information of a first user (such as user 112). The user information may be received by a plurality of sensors (such as the plurality of sensors 116) that tracks user activities of the first user over a specified time period. The circuitry may be configured to detect a baseline emotion of the first user over a first time period in the specified time period based on the user information. The circuitry 202 may be further configured to detect a first change in an emotional characteristic of the first user in the user information over a second time period in the specified time period, based on the detected baseline emotion of the first user. The circuitry 202 may be further configured to determine a dominant emotion of the first user based on the detected baseline emotion and the detected first change in the emotional characteristic of the first user in the user information. The circuitry 202 may be further configured to identify an emotional type of the determined dominant emotion. The emotional type is one of a positive emotional type or a negative emotional type. The circuitry 202 may be further configured to identify first content or action based on a specified emotion associated with the first content or action, the identified emotional type of the dominant emotion, the first change in the emotional characteristic of the first user, and the detected baseline emotion. The circuitry 202 may be further configured to output the identified first content or action to the first user, wherein the first content or action is output to change the emotional type of the dominant emotion from the negative emotional type to the positive emotional type.

In accordance with an embodiment, the circuitry 202 may be further configured to detect at least one emotional peak of the detected first change in the emotional characteristic of the first user based on a threshold intensity of the baseline emotion. The dominant emotion of the first user is determined further based on the detected at least one emotional peak.

In accordance with an embodiment, the user information received from the plurality of sensors 106 may include at least one of physiological and non-physiological features of the first user, and a plurality of image frames. Each image frame of the plurality of image frames may include an image of the first user. In accordance with an embodiment, the plurality of sensors 106 may include at least one of an imaging capturing device, an audio sensor, a biometric sensor, a heartbeat sensor, a blood-flow sensor, a motion sensor, a facial recognition sensor, or an Internet of things (IoT) sensor.

In accordance with an embodiment, the circuitry 202 may be further configured to generate an emotional storyboard that may include a timeline of a plurality of emotions of the first user over the specified of time. The plurality of emotions may include the dominant emotion and the baseline emotion. The circuitry 202 may be further configured to output the generated emotional storyboard to the first user.

In accordance with an embodiment, the circuitry 202 may be further configured to correlate trigger information in the user information with the determined dominant emotion of the first user. The trigger information comprises at least one of an event associated with the first user over the specified time period, second content visible to the first user at a time the plurality of sensors 106 tracks the user activities of the first user, and a second user associated with the first user over the specified time period. The circuitry 202 may be further configured to output the first content to the first user and update the generated emotional storyboard based on the correlation of the trigger information with the determined dominant emotion of the first user. In accordance with an embodiment, the emotional storyboard may include at least one of: the user information, date time information of an occurrence of the first change in the emotional characteristic, trigger information for the first change in the emotional characteristic, or the plurality of emotions of the at least one user. In accordance with an embodiment, the emotional storyboard may further include an avatar of the first user. Virtual emotions of the avatar correspond to the plurality of emotions of the first user.

In accordance with an embodiment, the memory may be further configured to store user-content preference information and user past emotional information of the first user. The circuitry 202 may be further configured to output at least one of video content clip or audio content as the first content based on at least one of the stored user-content preference information or the stored user past emotional information of the at least one user. In accordance with an embodiment, the circuitry 202 may be further configured to detect a second change in the emotional characteristic of the at least one user based on the output first content to the first user. The circuitry may be further configured to update the user past emotional information based on the detected second change in the emotional characteristic of the first user.

In accordance with an embodiment, the circuitry 202 may be further configured to predict an emotion of the first user based on the user-content preference information and the past emotional information of the first user. The circuitry 202 may be further configured to identify the first content for the first user based on the predicted emotion of the first user. In accordance with an embodiment, the circuitry may be further configured to detect a location of the first user and output at least one of an activity-to-do or a place-to-visit to first user based on the detected location.

In accordance with an embodiment, the circuitry 202 may be further configured to detect the baseline emotion and the dominant emotion of the first user based on a plurality of categories of user emotions. The plurality of categories of user emotions may include at least one of a sad emotion, a happy emotion, a calm emotion, an angry emotion, a fear emotion, a surprise emotion, a contempt emotion, a disgust emotion, a neutral emotion, or other variants of emotions. Each category of emotion of the plurality of categories of user emotions corresponds to one of the positive emotional type or the negative emotional type.

In accordance with an embodiment, the electronic apparatus is communicably coupled to an external apparatus that is configured to output the first content to the first user. The circuitry is further configured to change the first content based on the determined dominant emotion of the first user.

In accordance with an embodiment, the circuitry 202 may be further configured to receive role model information from the first user. The circuitry 202 may be further configured to extract, from a server, second content related to the role model information, wherein the second content includes at least an image of the role model. The circuitry 202 may be further configured to determine behavior of the role model in the extracted second content and recommend activity to the first user based on the determined behavior of the role model.

In accordance with an embodiment, the circuitry 202 may be further configured to calculate a positive activity index of the first user based on movement of the first user for the specified time period. The circuitry 202 may be further configured to output the calculated positive activity index to the first user.

In accordance with an embodiment, the electronic apparatus may be a wearable device. In accordance with an embodiment, the circuitry 202 may be further configured to detect a health status information of the first user based on the user information, and control output of the first content to the first user based on the detected health status of the first user, the specified emotion associated with the first content, the identified emotional type of the dominant emotion, the first change in the emotional characteristic of the first user, and the detected baseline emotion.

In accordance with an embodiment, the circuitry 202 may be further configured to transmit a signal to an external device based on the emotional type of the dominant emotion that corresponds to the negative emotional type. The signal may include the dominant emotion of the first user and a warning notification.

Various embodiments of the disclosure may provide a non-transitory computer readable medium and/or storage medium, and/or a non-transitory machine readable medium and/or storage medium with a machine code and/or a set of instructions stored thereon and executable by a machine and/or a computer to provide user consumable information independent of network connectivity. The set of instructions in the electronic apparatus 102 may cause the machine and/or computer to store user information of a first user. The user information may be received from a plurality of sensors that tracks user activities of the first user over a specified time period. A baseline emotion of the first user may be further detected over a first time period in the specified time period based on the user information. A first change in an emotional characteristic of the first user may be detected in the user information over a second time period in the specified time period, based on the detected baseline emotion of the first user. A dominant emotion of the first user may be determined based on the detected baseline emotion and the detected first change in the emotional characteristic of the first user in the user information. An emotional type of the determined dominant emotion may be identified, wherein the emotional type is one of a positive emotional type or a negative emotional type. Deductive information may be generated based on an association of the identified emotional type of the dominant emotion, the determined dominant emotion of the first user, the first change in the emotional characteristic of the first user, and the detected baseline emotion. Further, output of first content to the first user may be controlled based on a specified emotion associated with the first content and the generated deductive information such that the emotional type of the dominant emotion is inducible to the positive emotional type from the negative emotional type.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that includes a portion of an integrated circuit that also performs other functions.

The present disclosure may also be embedded in a computer program product, which includes all the features that enable the implementation of the methods described herein, and which when loaded in a computer system is able to carry out these methods. Computer program, in the present context, means any expression, in any language, code or notation, of a set of instructions intended to cause a system with information processing capability to perform a particular function either directly, or after either or both of the following: a) conversion to another language, code or notation; b) reproduction in a different material form.

While the present disclosure is described with reference to certain embodiments, it will be understood by those skilled in the art that various changes may be made and equivalents may be substituted without departure from the scope of the present disclosure. In addition, many modifications may be made to adapt a particular situation or material to the teachings of the present disclosure without departure from its scope. Therefore, it is intended that the present disclosure not be limited to the particular embodiment disclosed, but that the present disclosure will include all embodiments that fall within the scope of the appended claims.

What is claimed is:

1. An electronic apparatus, comprising:
    circuitry configured to:
        detect a first emotion of a first user over a first time period in a second time period based on user information, wherein
            the user information is received from a plurality of sensors that tracks a plurality of user activities of the first user over the second time period, and
            the plurality of sensors includes a biometric sensor, an image sensor, and an audio sensor;
        detect a first change in an emotional characteristic of the first user in the user information over a third time period in the second time period based on the detected first emotion of the first user;
        determine a second emotion of the first user based on the detected first emotion and the detected first change in the emotional characteristic of the first user in the user information;
        identify an emotion type of the determined second emotion as a negative emotion type;
        generate specific information based on an association of the identified emotion type of the determined second emotion, the determined second emotion of the first user, the detected first change in the emotional characteristic of the first user, and the detected first emotion, wherein the specific information is associated with the first user;
        control output of first content to the first user based on an emotion associated with the first content and the generated specific information, wherein the emotion type of the second emotion is inducible to a positive emotion type from the negative emotion type based on the output of the first content to the first user; and
        transmit a signal to an external device based on the identified emotion type of the determined second emotion that corresponds to the negative emotion type, wherein the signal comprises the determined second emotion of the first user and a warning notification.

2. The electronic apparatus according to claim 1, wherein the circuitry is further configured to detect at least one emotional peak of the detected first change in the emotional characteristic of the first user,
    the detection of the at least one emotional peak is based on a threshold intensity of the first emotion, and
    the second emotion of the first user is determined further based on the detected at least one emotional peak.

3. The electronic apparatus according to claim 1, wherein the user information received from the plurality of sensors comprises at least one of a plurality of features of the first user or a plurality of image frames.

4. The electronic apparatus according to claim 1, wherein the plurality of sensors further comprises at least one of a heartbeat sensor, a blood-flow sensor, a motion sensor, or a facial recognition sensor.

5. The electronic apparatus according to claim 1, wherein the circuitry is further configured to:
generate an emotional storyboard that comprises a timeline of a plurality of emotions of the first user over the second time period, wherein the plurality of emotions comprises the second emotion and the first emotion; and
output the generated emotional storyboard to the first user.

6. The electronic apparatus according to claim 5, wherein the circuitry is further configured to:
detect trigger information in the user information, wherein the trigger information comprises at least one of:
an event associated with the first user over the second time period,
second content visible to the first user at a time the plurality of sensors tracks the plurality of user activities of the first user, or
information associated with a second user, wherein the second user is associated with the first user over the second time period;
correlate the trigger information with the determined second emotion of the first user based on the detected trigger information and the detected first change in the emotional characteristic of the first user in the user information;
output the first content to the first user; and
update the generated emotional storyboard based on the correlation of the trigger information with the determined dominant second emotion of the first user.

7. The electronic apparatus according to claim 6, wherein the emotional storyboard comprises at least one of the user information, date-time information of an occurrence of the first change in the emotional characteristic, the trigger information for the first change in the emotional characteristic, or the plurality of emotions of the first user.

8. The electronic apparatus according to claim 7, wherein the emotional storyboard further comprises an avatar of the first user, and
virtual emotions of the avatar correspond to the plurality of emotions of the first user.

9. The electronic apparatus according to claim 1, further comprising
a memory configured to store user-content preference information of the first user and past emotion information of the first user,
wherein the circuitry is further configured to output at least one of video content or audio content, as the first content, based on at least one of the stored user-content preference information or the stored past emotion information of the first user.

10. The electronic apparatus according to claim 9, wherein the circuitry is further configured to:
detect a second change in the emotional characteristic of the first user based on the output first content to the first user; and
update the stored past emotion information based on the detected second change in the emotional characteristic of the first user.

11. The electronic apparatus according to claim 9, wherein the circuitry is further configured to:
predict an emotion of the first user based on the user-content preference information and the past emotion information of the first user; and
identify the first content for the first user based on the predicted emotion of the first user.

12. The electronic apparatus according to claim 1, wherein
the circuitry is further configured to:
detect a location of the first user; and
output information associated with at least one of an activity-to-do or a place-to-visit to the first user, and
the information is output based on the detected location.

13. The electronic apparatus according to claim 1, wherein
the circuitry is further configured to detect the first emotion and the second emotion of the first user based on a plurality of categories of user emotions,
the plurality of categories of user emotions comprises at least one of a sad emotion, a happy emotion, a calm emotion, an angry emotion, a fear emotion, a surprise emotion, a contempt emotion, a disgust emotion, a neutral emotion or other variants of emotions, and
each category of emotion of the plurality of categories of user emotions corresponds to one of the positive emotion type or the negative emotion type.

14. The electronic apparatus according to claim 1, wherein
the electronic apparatus is communicably coupled to an external apparatus that outputs the first content to the first user, and
the circuitry is further configured to change the first content based on the determined second emotion of the first user.

15. The electronic apparatus according to claim 1, wherein the circuitry is further configured to:
receive role model information from the first user, wherein the role model information indicates a role model preferred by the first user;
extract, from a server, second content related to the role model information, wherein the second content includes at least one image of the role model;
determine behavior of the role model based on the at least one image included in the extracted second content; and
recommend an activity to the first user based on the determined behavior of the role model.

16. The electronic apparatus according to claim 1, wherein
the plurality of sensors measures movement of the first user for the second time period, and
the circuitry is further configured to:
calculate an activity index of the first user based on the movement of the first user for the second time period; and
output the calculated activity index to the first user.

17. The electronic apparatus according to claim 1, wherein the electronic apparatus is a wearable device.

18. The electronic apparatus according to claim 1, wherein the circuitry is further configured to:
detect health status information of the first user based on the user information; and
control the output of the first content to the first user based on the detected health status information of the first user, the identified emotion type of the second emotion, the first change in the emotional characteristic of the first user, and the detected first emotion.

19. A method, comprising:
  in an electronic apparatus:
    detecting a first emotion of a user over a first time period in a second time period based on user information, wherein
      the user information is received from a plurality of sensors that tracks plurality of user activities of the user over the second time period; and
      the plurality of sensors includes a biometric sensor, an image sensor, and an audio sensor;
    detecting a change in an emotional characteristic of the user in the user information over a third time period in the second time period based on the detected first emotion of the user;
    determining a second emotion of the user based on the detected first emotion and the detected change in the emotional characteristic of the user in the user information;
    identifying an emotion type of the determined second emotion as a negative emotion type;
    generating specific information based on an association of the identified emotion type of the determined second emotion, the determined second emotion of the user, the detected change in the emotional characteristic of the user, and the detected first emotion, wherein the specific information is associated with the user;
    controlling output of content to the user based on an emotion associated with the content and the generated specific information, wherein the emotion type of the second emotion is inducible to a positive emotion type from the negative emotion type; and
    transmitting a signal to an external device based on the identified emotion type of the determined second emotion that corresponds to the negative emotion type, wherein the signal comprises the determined second emotion of the user and a warning notification.

* * * * *